(12) United States Patent
Stephan et al.

(10) Patent No.: US 8,426,130 B2
(45) Date of Patent: Apr. 23, 2013

(54) METHODS OF DIAGNOSING ALZHEIMER'S DISEASE AND MARKERS IDENTIFIED BY SET ASSOCIATION

(75) Inventors: Dietrich A. Stephan, Phoenix, AZ (US); Eric M. Reiman, Scottsdale, AZ (US); Jennifer Webster, Pheonix, AZ (US); Christopher B. Heward, late of, Mesa, AZ (US); Pamela Heward, legal representative, Mesa, AZ (US); Andreas Papassotiropoulos, Zurich (CH)

(73) Assignee: Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 12/148,728

(22) Filed: Apr. 21, 2008

(65) Prior Publication Data
US 2009/0249498 A1  Oct. 1, 2009

Related U.S. Application Data

(60) Provisional application No. 60/933,583, filed on Jun. 6, 2007, provisional application No. 60/925,638, filed on Apr. 20, 2007.

(51) Int. Cl.
*C12Q 1/68* (2006.01)
*C07H 21/02* (2006.01)
*A61P 25/28* (2006.01)
*A61K 48/00* (2006.01)

(52) U.S. Cl.
USPC ....... 435/6.11; 435/6.12; 435/6.16; 536/23.1; 514/17.8; 514/44 R

(58) Field of Classification Search ................ 435/6.11
See application file for complete search history.

(56) References Cited

U.S. PATENT DOCUMENTS

| | | | |
|---|---|---|---|
| 7,294,465 B2 | 11/2007 | Somlo et al. | |
| 2004/0067512 A1 | 4/2004 | Becker et al. | |
| 2004/0116682 A1 | 6/2004 | Cheikh et al. | |
| 2004/0265849 A1 | 12/2004 | Cargill et al. | |
| 2007/0054278 A1 | 3/2007 | Cargill | |
| 2007/0072184 A1 | 3/2007 | Nagy | |
| 2007/0077553 A1 | 4/2007 | Bentwich | |

OTHER PUBLICATIONS

GenBank Accession No. AC119504, last updated Oct. 13, 2002, located at <http://www.ncbi.nlm.nih.gov/entrez/viewerfcgi?db=nuccore&id=23928475>, last visited on Sep. 27, 2008, 28 pages.
International Search Report and Written Opinion mailed on Oct. 2, 2008, for PCT Application No. PCT/US08/61071 filed on Apr. 21, 2008, 13 pages.
NCBI ID: rs4420638, last updated Jan. 10, 2003, located at <http://www.ncbi.nlm.nih.gov/SNP/snp_ref.cgi?rs=4420638>, last visited on Sep. 27, 2008, 3 pages.
Reiman, E.M. et al. (Jun. 2007). "GAB2 Alleles Modify Alzheimer's Risk in APOE Epsilon4 Carriers," *Neuron* 54(5):713-720.
International Search Report and Written Opinion mailed Dec. 8, 2008, for PCT Application No. PCT/US08/61068 filed Apr. 21, 2008, 13 pages.
Mao, Y. at al. (Jul. 18, 2005). "A Novel Role for Gab2 in bFGF-Mediated Cell Survival During Retinoic Acid-Induced Neuronal Differentiation," *The Journal of Cell Biology* 170(2):305-316.
Misra, U. et al. (May 29, 1998). "Binding of Receptor-Recognized Forms of α2-Macroglobulin to the α2-Macroglobulin Signaling Receptor Activates Phosphatidylinositol 3-Kinase," *The Journal of Biological Chemistry* 273(22):13399-13402.

*Primary Examiner* — Valarie Bertoglio
(74) *Attorney, Agent, or Firm* — Yu Cai; Polsinelli Shughart PC

(57) ABSTRACT

The present disclosure relates to genetic markers and methods of diagnosing and screening for late-onset Alzheimer's disease (LOAD). As such, the disclosure encompasses a whole-genome association analysis of single nucleotide polymorphisms (SNPs) of which a number are located within the GRB2-associated binding protein 2 (GAB2) gene as well as other markers associated with other genes. The disclosure identifies two novel haplotypes within the GAB2 gene, i.e., a LOAD risk-enhancing and a LOAD risk-decreasing haplotype. These haplotypes modify LOAD risk differentially in combination with APOE alleles. Further encompassed are therapeutic methods and agents of decreasing the deterioration of cells associated with LOAD.

20 Claims, 10 Drawing Sheets

FIGURE 1

A
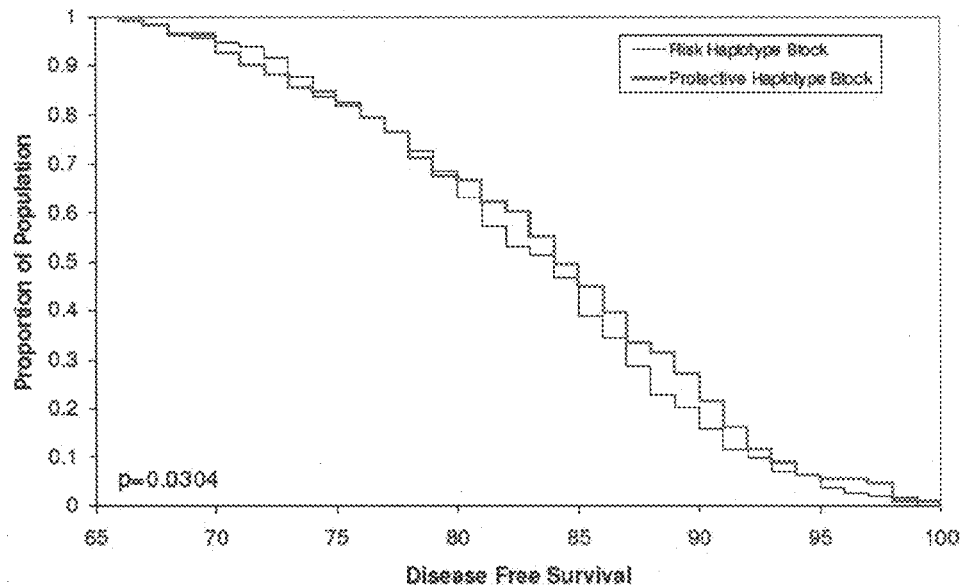
B
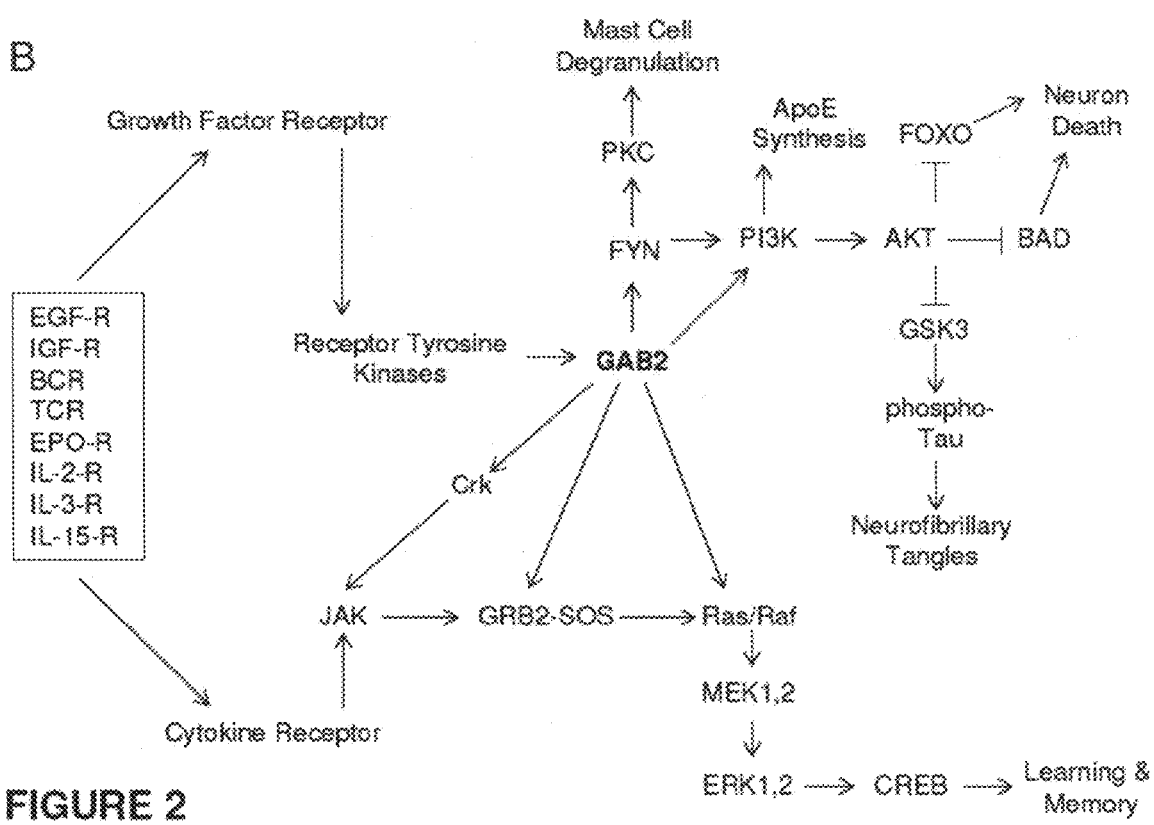
FIGURE 2

FIGURE 8

| SNP # (from Figure 1) | rs ID | Position on Chromosome | Position in Gene | SNP Alleles (on chip) | SNP Location (+/-) | Reference Sequence | On Affymetrix Chip ||| In Sequence (positive strand) |||
|---|---|---|---|---|---|---|---|---|---|---|---|---|
| | | | | | | | Risk Allele | Protective Allele | Neutral Allele | Risk Allele | Protective Allele | Neutral Allele |
| 5 | rs901104 | 77608147 | 4157 | C/T | + | T | C | T | C | C | T | C |
| 6 | rs1385600 | 77613814 | 9824 | C/T | - | A | T | C | T | A | G | A |
| 8 | rs1007837 | 77618724 | 14734 | A/G | - | T | A | G | A | T | C | T |
| 9 | rs2450130 | 77621105 | 17115 | A/C | - | T | A | C | A | T | C | T |
| 10 | rs2510054 | 77637307 | 33317 | A/G | + | G | G | A | G | G | A | G |
| 12 | rs2510038 | 77643682 | 39692 | C/T | + | T | C | T | C | C | T | C |
| 13 | rs2511170 | 77658230 | 54240 | A/G | + | A | A | G | G | A | G | A |
| 14 | rs4945261 | 77667908 | 63918 | A/G | + | G | G | A | G | G | A | G |
| 15 | rs7101429 | 77670615 | 66625 | A/G | - | A | A | G | A | A | G | A |
| 16 | rs10793294 | 77674051 | 70061 | G/T | - | C | T | G | G | A | C | C |
| 17 | rs4291702 | 77678896 | 74906 | C/T | - | A | C | T | C | G | A | G |
| 18 | rs11602622 | 77688478 | 84488 | A/G | - | T | A | G | A | T | C | T |
| 19 | rs10899467 | 77691705 | 87715 | G/T | - | A | G | T | G | C | A | C |
| 20 | rs2458640 | 77713504 | 109514 | A/C | + | C | A | C | A | A | C | A |
| 21 | rs10793302 | 77718609 | 114619 | C/T | - | G | C | T | C | G | A | G |
| 22 | rs2373115 | 77768798 | 164808 | G/T | - | A | G | T | G | C | A | C |

FIGURE 9

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Haplotype
<221> NAME/KEY: misc_feature
<222> LOCATION: 3, 7
<223> OTHER INFORMATION: n = A,T,C or G

<400> SEQUENCE: 1
tcngcantga ggtgtctt                                                 18

<210> SEQ ID NO 2
<211> LENGTH: 18
<212> TYPE: DNA
<213> ORGANISM: Artificial Sequence
<220> FEATURE:
<223> OTHER INFORMATION: Haplotype
<221> NAME/KEY: misc_feature
<222> LOCATION: 3, 7
<223> OTHER INFORMATION: n = A,T,C or G

<400> SEQUENCE: 2
ctnaagncag atcagacg                                                 18

<210> SEQ ID NO 3
<211> LENGTH: 18
<212> TYPE: DNA
<213> ORGANISM: Artificial Sequence
<220> FEATURE:
<223> OTHER INFORMATION: Haplotype
<221> NAME/KEY: misc_feature
<222> LOCATION: 3, 7
<223> OTHER INFORMATION: n = A,T,C or G

<400> SEQUENCE: 3
ctnaagncag agcagccg                                                 18

<210> SEQ ID NO 4
<211> LENGTH: 6006
<212> TYPE: DNA
<213> ORGANISM: Homo sapiens

<400> SEQUENCE: 4
atgagcggcg gcggcgacgt ggtgtgcacc ggctggctga ggaaatcgcc tcccgagaag      60
aagttgaggc gctatgcctg gaagaaacgc tggtttatcc tgcggagtgg ccggatgagc     120
ggtgacccag atgttctgga atactacaag aacgatcact ccaagaagcc tctgcggatc     180
atcaacctga acttctgtga gcaggtagat gcaggcctga cctttaacaa gaaggagctg    240
caggatagtt ttgtgtttga catcaagacc agtgaacgca ccttttacct ggtggctgag     300
acagaagagg acatgaataa gtgggtccag agcatctgcc agatctgtgg cttcaatcag    360
```

```
gctgaggaga gcacagactc cctgagaaat gtttcctcag ccggtcatgg cccccgctct    420
tctccagctg agctcagcag ctctagccag caccttctcc gagagcgcaa gtcctcagcc    480
ccatcacact ccagccagcc aactctgttc acgtttgaac ccctgtgtc aaaccacatg     540
cagcccacct tgtccaccag cgcacctcag gagtatctct acttgcacca gtgcataagc    600
cgaagagcag aaaatgcaag gagtgccagc ttctctcagg gcaccagagc ctcttttctc    660
atgaggagtg acacagctgt acaaaaactt gcccagggca atggacactg tgtcaacggg    720
atcagtggtc aagtccatgg cttctatagc cttcccaagc cgagccggca caatacagaa    780
ttcagagaca gtacctacga cctcccccgc agcctggcct cccatggcca ccaagggc      840
agcctcacag gctccgagac agataatgag gatgtgtaca ccttcaagac gcccagcaac    900
accctgtgca gggagttcgg ggacctcctg gtagacaata tggatgttcc ggccacccca    960
ctctcagcct accagatccc taggacattc actctggaca aaaaccacaa tgccatgaca    1020
gtggccactc ctggggactc agccatagct cccccacccc gccccccaa gccaagtcag     1080
gcagaaacac ctcgatgggg cagtcctcag cagagaccgc caatcagtga aaatagcaga    1140
tctgtcgctg ccaccatccc cagacgcaac accctccctg caatggacaa cagccgactt    1200
caccgagctt cttcctgtga gacctacgag taccacagc gtggtggaga gagtgcaggc     1260
cggtctgctg aatccatgag tgatggagtt ggctcttcc tgccagggaa aatgattgtg      1320
ggccgatcgg acagcaccaa ttctgaagac aactatgtgc ccatgaatcc aggttcttcc    1380
accctgttgg ccatggaacg agcaggtgat aattcccaga gcgtctacat cccaatgagc    1440
ccaggggccc atcactttga ctcacttggc tacccatcaa caacccttcc tgtgcaccga    1500
ggccccagca gaggaagtga gattcagcca cccctgtca accgcaacct caaacctgat     1560
cggaaagcaa agccaacacc acttgacctg aggaacaaca ccgtcatcga tgaactcccc    1620
ttcaagtcac ctatcaccaa gtcttggtct agggccaacc acaccttcaa ctccagctcc    1680
tcccagtact gccgccccat ctccacccag agcatcacca gcacagactc aggagacagc    1740
gaagagaact atgtccctat gcaaaaccca gtgtctgcat ctcccgttcc cagtggcacg    1800
aacagtcctg cccctaagaa gagcaccggc agcgttgatt atctggccct ggacttccag    1860
ccgagctccc caagcccca ccgcaagcca tctacttcat ccgtcacctc tgatgagaag     1920
gtggactacg ttcaggtgga caaggagaag acccaggccc tgcagaacac catgcaggag    1980
tggacagacg tgcggcagtc ctcagagcct tccaagggtg ccaagctgtg atgagagggc    2040
caccgcagag cccaggaggc agcatctcca gagctggccc ttcccatctc ccctctcccc    2100
tctcccgttc ttcctcccat ccacctcctc tctactctgc cagtctcagc cttcaaagca    2160
cttgacatca gggaccctga acccttcccc tgggaggtga gggcctgatc aaggcacctc    2220
ctctgcccac tcggggccca gctgtgattt ttatcagtaa tggccatgcc tccacccacc    2280
ttagttagga gctacttcca aaaagcatcc ttcagcctct tcctgtcctt tagacctgac    2340
tctctaccag atgtttggag ggaagggctg gggctctgag ccagattcca cacctcacgt    2400
tcagtcacag ccctcagcta tcttccctcc ggccactggg ctacctctcc ttcagtccca    2460
gaagacaagt ctcaccaacc cagggagtca aggaccagca aaccaaagtg gataatggac    2520
tttttcattc ctgttttctt tggcaggaga aagcaaggc cactaaaaga ggagatggtg      2580
gagacggagg ctcagcagtg gtcttgaggg gtaaaggact tagatgccca gatgaagagg    2640
gaaagctgac atctgcaggg aacccacttt gaggctgagg ccatggcagg acagctgctg    2700
tggggtgcag aggcagaaga tgaaggacaa aaggaaggga aaactgatgg ccaacctaga    2760
```

```
gcagcaagga gcagggcttg gagctcgggt ggtggagatg acaaggacac tgtgggtct    2820 gggtccccag aactctggag ctacaggcca ctctaggccc aagggctagt cctcttcccc    2880
agtcccctca gaggcccccg ccagccccac cttgaaagca gcatacaggg aaggcttgg    2940 accaagctgg gcgaccaagc acatgggca ggaacacatg gtaaaggggt ggggaatatg    3000
ggagggagtg tggtgtggat ggggggtgatg cagggactga ggggaaccct gggacaggca    3060
caggctgggc agaggcacag ggcagtgcag ggactctgc agtggggtcg ggaagtgagt    3120
ttctttgcag tgagcagtgc agtggaagtc gggcacagag gtagcagaca gatgtgaagc    3180
agtggtgaag gccatgtagc aagtggggaa atacatccaa agggcctggg agttgggggg    3240
tgcccaacgc aatccttggg ggtgcagggt ggagcagaaa gtgaaggagg gacacgtgca    3300
agagtggtgt gcatggtggt gtgacatgag gaccgttcct aggatgggac agtgggtcag    3360
gcaggacaag gagaaagcag ggcagaatga tgcctagagg accacatcag gcatggctga    3420
cagcttgtgc ccatgggctg tggcgtatgt cagatcgcag ggtaggaacg agtctggcct    3480
ggtgccggcc cagtgtttcc tcagctcatc cgccctctgt tgctccctag cattccagga    3540
gccatcttgg actctcctcc ccaggtttga aaggccatca gattagcagg gacggggtgt    3600
agggcatcac ccaaggttcc ttctcttaaa ctaagggtgg gggatctgaa tgttttatg    3660 ttgactgttc ttgactaaat tttcaagagt ttcagaagca acaggacaga ccagacgttt    3720
cattctaccc tggggcgaac agaacttctt cctcccaaac aatgacttcc tgccatgttt    3780 gatgggaca gctaccactg tcctctgccc ccattcccct ttcagctccc atgagcatgc    3840
atagttcacc agaccaatgg cctagccatt ctctaagtcc catcctggaa gaagttattt    3900
cttcaagagc tgcacctctc ctcctagcat tagtttagat caactcaagg agtatttatt    3960
aatggctgct gtctccagtt tctggggtta agcactaagg acacaagaat caatcagacc    4020
ttctccctga acttaagata gccacaatca gaaaaaggac aaggacatga gacagtggtg    4080
atggccatca gacagagact tcaaatgctg atggagggca gaggaagtac ttagggaggt    4140
tggtgtcaga ggcaggagtg ggggatcagg gaaggtggat tctaggaaaa gggagtgcct    4200
gaggtaggcc ttagaagggg atgagtcaga tttttacaga ggaggagggc agggcttggg    4260
tccagtggag gaagaaggaa ggagaggctt ggaaagcctt tgtgtcttggg aaaaaaaggc    4320 cttttgagcat atgggtccag ccactcagaa gtgcaggggc catgccttgg tgttccaata    4380
agtgaatgga agcagtggtg gtagctacac tgggcagagt tggcagggtg ctggttcact    4440
ctgcccagcc ctgaatgtgt gccttaaagg ccccctacaa ggggcccat acgacagagc    4500 ttttaactgg tgccttccct gtacccgcag cagccacaag tgggcccaga ctattgcagc    4560
ctcccataaa catgtgagca tgttctgagt gtgccatgat gtgagtggac ctggctggaa    4620
tcttcggaga gcgactgagg tgttcaaatc gaatctccca ggaggcttcc ttccagcccc    4680
ctattctggt aactaccagg aggcttcctt ccagccccct attctggtaa ctaccaaaat    4740
ccctcgggtg caagtgtagg ggtagagatg gaaggatgag aggtgaaatt gacctttga    4800 aagcaaagct ctggctcaca ggccccaaac taccagccgt atctagcata tccccaccct    4860
ccacccacta cctcctccaa caaaggagtc aactcagttg aaaaaactgg tcctttggcc    4920
tatccatggg tcaaagtcca cctctcctgg gggcctggag aggactgagc ctacggaaag    4980
gggatacctt cccactcagc actgcttcac acaggccccc tgcctggggc tctccaagga    5040
gccttcttca cccacttcca gctccacttc tgcaaggtta agtcaagtga aacgatgag    5100 aaatagggag atggtgtctc cttaagtcct tgatctgcct gtctgtggaa tgggaggttg    5160
```

| | | |
|---|---|---|
| gattagctgc gctgaggtcc catccacagc tggtgctcag ctgcttgaag gggagactcc | 5220 |
| ctcctctgta acttctttct gggggattgg ggtgggcagt acctatcccc agtcccctcc | 5280 |
| tagcttgact ttagtggttt ccaatgtaga agttaacaaa gtatgcccca ttcctgtgac | 5340 |
| aaaagcacaa ccattctgaa gttactggag catgggctca gctcatcctc cctctggccc | 5400 |
| cttctcccat ggggacatct cggcccagca ccctatcccc atttccagag ttcttccttc | 5460 |
| cccatctggg ccttcataaa atgcagggga agccagactg gtctcaggag cgctaaagcc | 5520 |
| cttccgtggg gggtcgtctt tctgggacta gccctgctgt ttaggacctg ggaccacaat | 5580 |
| ggggtacctg ccgagggggt ccccaagaga tccaggctgt catgtgattt atggtggcat | 5640 |
| gtgttgtgta tttgttggct acttgtgtct tgaaatctag aattatttca cgcagaattg | 5700 |
| tcactgtttg tcaggaagag aaaatgggct agtggaagcc cagtcttgag ttcttgtctt | 5760 |
| gttaccattt aaaattgaca tttaatttt aaatcactgt tggtgcctaa tcacttaagt | 5820 |
| tattaattta ttctgttgta ttcttttttt taaattgtaa catatttatc cggtgggtgg | 5880 |
| gacaggagtg tgttcaagtg ggtcatgttt ttgctgtggt gacacatggt acaggcttgg | 5940 |
| agcttgcagg tcccttttcta ctgtggtgtt ggagcaggac aataaagtcc actagaaatg | 6000 |
| cacccc | 6006 |

<210> SEQ ID NO 5
<211> LENGTH: 676
<212> TYPE: PRT
<213> ORGANISM: Homo sapiens

<400> SEQUENCE: 5

```
Met Ser Gly Gly Gly Asp Val Val Cys Thr Gly Trp Leu Arg Lys Ser
 1               5                  10                  15

Pro Pro Glu Lys Lys Leu Arg Arg Tyr Ala Trp Lys Lys Arg Trp Phe
            20                  25                  30

Ile Leu Arg Ser Gly Arg Met Ser Gly Asp Pro Asp Val Leu Glu Tyr
        35                  40                  45

Tyr Lys Asn Asp His Ser Lys Lys Pro Leu Arg Ile Ile Asn Leu Asn
    50                  55                  60

Phe Cys Glu Gln Val Asp Ala Gly Leu Thr Phe Asn Lys Lys Glu Leu
65                  70                  75                  80

Gln Asp Ser Phe Val Phe Asp Ile Lys Thr Ser Glu Arg Thr Phe Tyr
                85                  90                  95

Leu Val Ala Glu Thr Glu Glu Asp Met Asn Lys Trp Val Gln Ser Ile
            100                 105                 110

Cys Gln Ile Cys Gly Phe Asn Gln Ala Glu Glu Ser Thr Asp Ser Leu
        115                 120                 125

Arg Asn Val Ser Ser Ala Gly His Gly Pro Arg Ser Ser Pro Ala Glu
    130                 135                 140

Leu Ser Ser Ser Ser Gln His Leu Leu Arg Glu Arg Lys Ser Ser Ala
145                 150                 155                 160

Pro Ser His Ser Ser Gln Pro Thr Leu Phe Thr Phe Glu Pro Pro Val
                165                 170                 175

Ser Asn His Met Gln Pro Thr Leu Ser Thr Ser Ala Pro Gln Glu Tyr
            180                 185                 190

Leu Tyr Leu His Gln Cys Ile Ser Arg Arg Ala Glu Asn Ala Arg Ser
        195                 200                 205

Ala Ser Phe Ser Gln Gly Thr Arg Ala Ser Phe Leu Met Arg Ser Asp
    210                 215                 220
```

```
Thr Ala Val Gln Lys Leu Ala Gln Gly Asn Gly His Cys Val Asn Gly
225                 230                 235                 240

Ile Ser Gly Gln Val His Gly Phe Tyr Ser Leu Pro Lys Pro Ser Arg
                245                 250                 255

His Asn Thr Glu Phe Arg Asp Ser Thr Tyr Asp Leu Pro Arg Ser Leu
            260                 265                 270

Ala Ser His Gly His Thr Lys Gly Ser Leu Thr Gly Ser Glu Thr Asp
        275                 280                 285

Asn Glu Asp Val Tyr Thr Phe Lys Thr Pro Ser Asn Thr Leu Cys Arg
    290                 295                 300

Glu Phe Gly Asp Leu Leu Val Asp Asn Met Asp Val Pro Ala Thr Pro
305                 310                 315                 320

Leu Ser Ala Tyr Gln Ile Pro Arg Thr Phe Thr Leu Asp Lys Asn His
                325                 330                 335

Asn Ala Met Thr Val Ala Thr Pro Gly Asp Ser Ala Ile Ala Pro Pro
            340                 345                 350

Pro Arg Pro Pro Lys Pro Ser Gln Ala Glu Thr Pro Arg Trp Gly Ser
        355                 360                 365

Pro Gln Gln Arg Pro Pro Ile Ser Glu Asn Ser Arg Ser Val Ala Ala
    370                 375                 380

Thr Ile Pro Arg Arg Asn Thr Leu Pro Ala Met Asp Asn Ser Arg Leu
385                 390                 395                 400

His Arg Ala Ser Ser Cys Glu Thr Tyr Glu Tyr Pro Gln Arg Gly Gly
                405                 410                 415

Glu Ser Ala Gly Arg Ser Ala Glu Ser Met Ser Asp Gly Val Gly Ser
            420                 425                 430

Phe Leu Pro Gly Lys Met Ile Val Gly Arg Ser Asp Ser Thr Asn Ser
        435                 440                 445

Glu Asp Asn Tyr Val Pro Met Asn Pro Gly Ser Ser Thr Leu Leu Ala
    450                 455                 460

Met Glu Arg Ala Gly Asp Asn Ser Gln Ser Val Tyr Ile Pro Met Ser
465                 470                 475                 480

Pro Gly Ala His His Phe Asp Ser Leu Gly Tyr Pro Ser Thr Thr Leu
                485                 490                 495

Pro Val His Arg Gly Pro Ser Arg Gly Ser Glu Ile Gln Pro Pro Pro
            500                 505                 510

Val Asn Arg Asn Leu Lys Pro Asp Arg Lys Ala Lys Pro Thr Pro Leu
        515                 520                 525

Asp Leu Arg Asn Asn Thr Val Ile Asp Glu Leu Pro Phe Lys Ser Pro
    530                 535                 540

Ile Thr Lys Ser Trp Ser Arg Ala Asn His Thr Phe Asn Ser Ser Ser
545                 550                 555                 560

Ser Gln Tyr Cys Arg Pro Ile Ser Thr Gln Ser Ile Thr Ser Thr Asp
                565                 570                 575

Ser Gly Asp Ser Glu Glu Asn Tyr Val Pro Met Gln Asn Pro Val Ser
            580                 585                 590

Ala Ser Pro Val Pro Ser Gly Thr Asn Ser Pro Ala Pro Lys Lys Ser
        595                 600                 605

Thr Gly Ser Val Asp Tyr Leu Ala Leu Asp Phe Gln Pro Ser Ser Pro
    610                 615                 620

Ser Pro His Arg Lys Pro Ser Thr Ser Ser Val Thr Ser Asp Glu Lys
625                 630                 635                 640

Val Asp Tyr Val Gln Val Asp Lys Glu Lys Thr Gln Ala Leu Gln Asn
                645                 650                 655
```

```
Thr Met Gln Glu Trp Thr Asp Val Arg Gln Ser Ser Glu Pro Ser Lys
            660                 665                 670

Gly Ala Lys Leu
        675
```

METHODS OF DIAGNOSING ALZHEIMER'S DISEASE AND MARKERS IDENTIFIED BY SET ASSOCIATION

METHODS OF DIAGNOSING ALZHEIMER'S DISEASE AND MARKERS IDENTIFIED BY SET ASSOCIATION

CROSS REFERENCE TO RELATED APPLICATIONS

This application claims the benefit of U.S. Provisional Application Ser. No. 60/933,583, filed Jun. 6, 2007, and U.S. Provisional Application Ser. No. 60/925,638, filed Apr. 20, 2007, both of which are hereby incorporated by reference in their entireties.

INCORPORATION OF SEQUENCE LISTING

The entire contents of a paper copy of the "Sequence Listing" and a computer readable form of the sequence listing on diskette, containing all sequences are herein incorporated by reference.

BACKGROUND

1. Field

The present disclosure relates to genetic markers, compositions for the detection of genetic markers and methods of diagnosing and screening for Alzheimer's disease (AD). Further encompassed are therapeutic methods and agents for decreasing the deterioration of cells associated with AD and methods of screening such agents.

2. Related Art

Disorders of the brain are serious medical conditions causing disability and diminished quality of life. Neurological damage is largely irreversible and thus early diagnosis and close monitoring are critical to the successful treatment of patients. Alzheimer's disease (AD) is a neurodegenerative disease associated with progressive memory loss and cognitive dysfunction. It is associated with abnormal clumps (amyloid plaques) and tangled bundles of fibers (neurofibrillary tangles) in the brain which are considered signs of AD. An estimated 4 million Americans have AD. By the year 2030 approximately 1 in every 80 persons in the U.S. will have AD.

Familial Alzheimer's disease (FAD) is known to be inherited. In affected families, members of at least two generations have had the disease. FAD is rare, accounting for less than 1% of all cases of AD. FAD has an earlier onset, i.e., about 40 years of age and can be observed to run in families.

Early-onset Alzheimer's disease (EOAD) is a rare form of Alzheimer's disease in which individuals are diagnosed with the disease before age 65. Less than 10% of all Alzheimer's disease patients have EOAD. Younger individuals who develop Alzheimer's disease exhibit more of the brain abnormalities that are normally associated with Alzheimer's disease. EOAD is usually familial and follows an autosomal dominant inheritance pattern. To date, mutations in three genes including amyloid precursor protein (APP) on chromosome 21, presenilin 1 (PSEN1) on chromosome 14 and presenilin 2 (PSEN2) on chromosome 1 have been identified in families with EOAD. Mutations in the APP, PSEN1 and PSEN2 genes account for about 50% of the disease. Most of the pathogenic mutations in the APP and presenilin genes are associated with abnormal processing of APP, which leads to the overproduction of toxic Aβ-1-42. Down syndrome patients, who have three copies of chromosome 21 which includes the APP gene, begin to develop the characteristic senile plaques and tau tangles at the ages of 30 and 40 (M. Ilyas Kamboh (2004), Molecular Genetics of Late-Onset Alzheimer's Disease, *Annals of Human Genetics* 68(4):381-404).

Late-onset Alzheimer's disease (LOAD) is the most common form of Alzheimer's disease, accounting for about 90% of cases and usually occurring after age 65. LOAD strikes almost half of all individuals over the age of 85 and may or may not be hereditary. It is a complex and multifactorial disease with the possible involvement of several genes. Genome-wide linkage or linkage disequilibrium studies on LOAD have provided informative data for the existence of multiple putative genes for AD on several chromosomes, with the strongest evidence on chromosomes 12, 10, 9 and 6. LOAD cases tend to be sporadic, wherein there is no family history of the disease. Genetic susceptibility at multiple genes and interaction between these genes as well as environmental factors are most likely responsible for the etiology of LOAD. Twin data on incident cases indicates that almost 80% of the LOAD risk is attributable to genetic factors. The Apolipoprotein E (APOE) gene on chromosome 19q13 has been identified as a strong risk factor for LOAD. In fact, the APOE-ϵ4 allele has been established as a strong susceptibility marker that accounts for nearly 30% of the risk in late-onset AD. More specifically, three variants of APOE, encoded by codons 112 and 158, have been found to modify the risk of LOAD. As compared to the common APOE-ϵ3 allele (codon 112=Cys and codon 158=Arg), the APOE-ϵ4 allele (codon 112=Arg and codon 158=Arg) increases the risk of AD, while the APOE-ϵ2 allele (codon 112=Cys and codon 158=Cys) decreases the risk of AD. The effect of the APOE-ϵ4 allele is dose related, wherein one or two copies of the APOE-ϵ4 allele are associated with 3-fold or 15-fold risk, respectively. However, the effect of the APOE-ϵ4 allele on AD risk appears to decline with increasing age (M. Ilyas Kamboh (2004), supra).

From the time of diagnosis, people with AD survive about half as long as those of similar age without dementia. Medicare costs for beneficiaries with AD were $91 billion in 2005 and may increase to as much as $160 billion in 2010. Finding a treatment that could delay the onset by five years could reduce the number of individuals with AD by nearly 50 percent after 50 years. Drug development for AD is very active and sensitive diagnostic and screening technologies could identify patients for therapy and monitor their response. Improved diagnostic tools for AD would thus be a significant advancement to drug development for this disease and would also provide a means to guide therapeutic decision making thus improving outcomes and reducing unnecessary exposure of patients to costly medications with unwanted side effects.

SUMMARY

The present disclosure relates to genetic markers and methods of diagnosing and screening for late-onset Alzheimer's disease (LOAD). As such, the disclosure encompasses a whole-genome association analysis of single nucleotide polymorphisms (SNPs) of which a number are located within the GRB2-associated binding protein 2 (GAB2) gene and other genes as set forth in Table 7. The disclosure identifies two novel haplotypes within the GAB2 gene, i.e., a LOAD risk-enhancing and a LOAD risk-decreasing haplotype as well as other markers disclosed on Table 7 associated with LOAD risk. These haplotypes and some of the markers modify LOAD risk differentially in combination with APOE alleles. Further encompassed are therapeutic methods and agents of decreasing the deterioration of cells associated with LOAD.

One aspect of the disclosure provides a method of assigning a subject to a late onset Alzheimer's disease (LOAD) risk group wherein the method includes providing a biological sample from the subject, detecting a marker in the biological sample selected from a group comprising: a marker associated with a haplotype of GAB2 associated with LOAD and the markers in Table 7; and assigning the subject to the late onset Alzheimer's disease (LOAD) risk group based upon the presence or absence of the marker. The method involves directly or indirectly detecting the presence or absence of the marker. In one embodiment, the marker is associated with increased risk of LOAD and the subject is assigned to a high LOAD risk group if the subject has the marker. Thus, the presence of this haplotype indicates that the subject is at an increased risk of developing LOAD. As such, the haplotype of GAB2 has the SNP haploblock identified by SEQ ID NO: 2. In another embodiment, the marker is associated with a decreased risk of LOAD and the subject is assigned to a low LOAD risk group if the subject has the marker. Thus, the presence of this haplotype indicates that the subject is at a decreased risk of developing LOAD. As such, the haplotype of GAB2 has the SNP haploblock identified by SEQ ID NO: 1. In addition, the subject usually carries an apolipoprotein E allele associated with increased LOAD risk regardless of the haplotype. Most often, the subject will carry APOE-ε4, an allele commonly associated with LOAD. In certain instances, the subject will carry the APOC-1a SNP rs4420638.

The disclosure contemplates that the marker is detected by a method including but not limited to nucleic acid hybridization, antibody binding, activity assay, polymerase chain reaction (PCR), S1 nuclease assay and via gene chip. For example, the marker can be detected by nucleic acid hybridization using at least one hybridization probe specific to a SNP specific, by way of example, to the SNP haploblock identified by SEQ ID NO: 1 or SEQ ID NO: 2.

Another aspect of the disclosure provides for an isolated and/or recombinant nucleic acid encoding the amino acid sequence of GAB2-R2, wherein the amino acid sequence codes for a GAB2 protein that is associated with increased risk of LOAD in individuals that carry the APOE-ε4 allele. The corresponding nucleotide sequence is provided by GAB2-R1. The nucleic acid can be provided in combination with an expression vector which can be transformed into a host cell such that the host cell expresses the GAB2 protein that is associated with increased risk of LOAD.

Another aspect of the disclosure provides for an isolated and/or recombinant nucleic acid encoding the amino acid sequence of GAB2-P2, wherein the amino acid sequence codes for a GAB2 protein that is associated with decreased risk of LOAD in individuals that carry the APOE-ε4 allele. The corresponding nucleotide sequence is provided by GAB2-P1. The nucleic acid can be provided in combination with an expression vector which can be transformed into a host cell such that the host cell expresses the GAB2 protein that is associated with decreased risk of LOAD. This protein has a protective effect and thus, it decreases the likelihood of developing LOAD.

The disclosure further encompasses a set of molecular probes for detection, including at least two probes capable of detecting, directly or indirectly, at least two markers disclosed herein associated with increased or decreased risk of LOAD, wherein the molecular probes are not associated with a microarray of greater than 1000 elements. In certain embodiments, at least one of the probes is specific for a marker associated with increased risk of LOAD and at least one other probe is specific for a marker associated with decreased risk of LOAD. Thus, the probes are able to detect directly or indirectly the presence or absence of the marker and are useful for diagnosis, monitoring and risk assessment of LOAD.

Another aspect of the disclosure provides a method of decreasing neuronal cell deterioration in a subject with dementia (e.g., LOAD), wherein the method includes administering a construct with a nucleic acid of SEQ ID NO: 4 or a fragment thereof to the subject. The nucleic acid codes for GAB2 and the construct includes a recombinant vector in order to transform the construct into cells or tissues of the subject such that the protein can be expressed. In one embodiment, the construct is provided to the subject in form a pharmaceutical composition. Thus, the construct or pharmaceutical composition thereof can be used to treat LOAD. Alternatively, the disclosure provides for a method of decreasing neuronal cell deterioration in a subject with dementia, wherein the method includes administering a polypeptide of SEQ ID NO: 5 or a fragment thereof to the subject. The polypeptide codes for GAB2 which can be administered in form of a pharmaceutical composition. Thus, the protein or pharmaceutical composition thereof can be used to treat LOAD. The subject to be treated for LOAD usually carries an apolipoprotein E allele such as APOE-ε4. In a preferred embodiment, the subject is a human or other mammal.

The disclosure further includes a method of decreasing or preventing neuronal cell deterioration in a subject at risk for LOAD, wherein the method includes administering a compound that modulates PI3K or ERK activity. Such a compound can mimic the function of GAB2 which is encoded by the nucleic acid sequence of SEQ ID NO: 4. The corresponding amino acid sequence is encoded by SEQ ID NO: 5.

The disclosure also encompasses a method of decreasing or preventing neuronal cell deterioration in a subject at risk for LOAD, wherein the method includes administering an siRNA specific for the haplotype of GAB2 with the SNP haploblock identified by SEQ ID NO: 2. Herein, the subject is heterozygous for the haplotype of GAB2 with the SNP haploblock identified by SEQ ID NO: 2. In a preferred embodiment, the subject is a human or other mammal.

Yet, another aspect of the disclosure provides a method of treating or preventing neuronal cell deterioration in a subject at risk for LOAD, wherein the method includes isolating stem cells from the subject; contacting the stem cells with a nucleic acid encoding GAB2 or a fragment thereof which is not the haplotype of GAB2 with the SNP haploblock identified by SEQ ID NO: 2, wherein the nucleic acid homologously recombines with at least one genomic copy of GAB2 in the stem cells; and contacting the subject with the stem cells to treat or prevent neuronal cell deterioration. Alternatively, the disclosure provides a method of treating or preventing neuronal cell deterioration in a subject at risk for LOAD, wherein the method includes isolating stem cells from the subject; contacting the stem cells with a nucleic acid encoding GAB2 or a fragment thereof which is the haplotype of GAB2 with the SNP haploblock identified by SEQ ID NO: 1, wherein the nucleic acid homologously recombines with at least one genomic copy of GAB2 in the stem cells; and contacting the subject with the stem cells to treat or prevent neuronal cell deterioration. The subject usually carries an apolipoprotein E allele associated with increased. LOAD risk such as the APOE-ε4 allele.

Still, another aspect of the disclosure provides a method for screening for a therapeutic agent effective to inhibit development of cell deterioration associated with dementia, wherein the method includes incubating neuronal cells in vitro with a mixture of PI3K and an agent to be tested; measuring PI3K activity; comparing the activity to PI3K activity in the absence of the agent to be tested; and identifying the therapeutic agent by indication of PI3K activity in the presence of the agent. The therapeutic agent can inhibit the cell deterioration associated with dementia such as LOAD.

The disclosure further contemplates a non-human transgenic animal with a genome including. SEQ ID NO: 1 or SEQ ID NO: 2 in association with a gene for GAB2. The non-human animal can be used as a disease model for screening therapeutic compounds for treatment of LOAD.

In yet another aspect, the disclosure provides a method for screening for a therapeutic agent effective to inhibit development of cell deterioration associated with dementia, wherein the method includes providing a transgenic animal with a genome including SEQ ID NO: 1 or SEQ ID NO: 2 in association with a gene for GAB2; administering to the transgenic animal an agent to be tested for its effectiveness in treating or preventing the cell deterioration associated with dementia; and assessing the effectiveness of the agent. This method can be used to screen for therapeutic agents that are effective in the treatment and prevention of LOAD.

BRIEF DESCRIPTION OF THE DRAWING FIGURES

The present disclosure is best understood when read in conjunction with the accompanying figures, which serve to illustrate the preferred embodiments. It is understood, however, that the disclosure is not limited to the specific embodiments disclosed in the Figures.

The patent or application file contains at least one drawing executed in color. Copies of this patent or patent application publication with color drawings will be provided by the Office upon request and payment of the necessary fee.

FIG. 1 depicts the Linkage Disequilibrium (LD) structure, haplotype significance levels (p-values), and Odds Ratios (ORs) 95% CIs for the region encompassing GAB2 on chromosome 11q14.1. LD mapping of the 300 kb surrounding the APOE locus was performed importing genotypes into the HaploView program version 3.33. A strong LD (measured by D' statistic) represents the likelihood that two genetic markers are inherited together. Pair-wise LD values (as measured by D'), reflecting the likehihood that two genetic markers are inherited together, were calculated for each pair of SNPs across the 300 kb interval using the Haploview software and plotted. Following the standard Haploview color scheme, the gradation bar at the bottom of the figure provides a key for D' versus color. SNP numbers correspond to the following dbSNP ID identification numbers: 1:rs579711, 2:rs977978, 3:rs637149, 4:rs977977, 5:rs901104, 6:rs1385600, 7:rs11237419, 8:rs1007837, 9:rs2450130, 10:rs2510054, 11:rs11237429, 12:rs2510038, 13:rs2511170, 14:rs4945261, 15:rs7101429, 16:rs10793294, 17:rs4291702, 18:rs11602622, 19:rs10899467, 20:rs2458640, 21:rs10793302, 22:rs2373115, 23:rs12280198, 24:rs12287010, 25:rs17136630, 26:rs4945276, 27:rs1996172, 28:rs7395344, 29:rs11237522, and 30:rs7950813. In all three cohorts, there was a GAB2 haplotype associated with higher LOAD risk, a haplotype associated with lower risk, and a haplotype unrelated to LOAD risk in APOE ε4 carriers.

FIG. 2 shows the following:
A—Kaplan-Meier plot for carriers of the risk-modifying haplotypes of GAB2.
B—Signaling Cascasde for GAB2: GAB2 is an important scaffolding molecule that mediates signaling from growth factor and cytokine receptors to tau phosphorylation, ApoE synthesis, mast cell degranulation and learning and memory.

FIG. 3 illustrates a map that depicts the various SNPs: PupaSNP was used to identify known SNPs that were likely to play a significant physiological role due to their location in exonic splicing enhancers (ESEs) or triplex forming regions (TRPs), both of which provide for sequence specific regulation of expression and splicing. The four non-synonymous coding SNPs are the most likely candidates for causing functional variance.

FIG. 4A-D depicts GAB2 immunoreactivity in LOAD hippocampus and posterior cingulate cortex using an affinity purified goat polyclonal antibody directed against a C-terminal epitope of GAB2 (Santa Cruz Biotechnology, Santa Cruz, Calif.). Blocks were obtained from rapid autopsy LOAD cases (<3 hours postmortem) (N=5). Hippocampus sections derived from blocks that were fixed for 24 hours in 4% paraformaldehyde and sectioned at 40 cm on a freezing microtome. Posterior cingulate sections derived from snap-frozen blocks that were sectioned at 6 μm on a cryostat. Immunohistochemical protocols were as described by Li et al. (Neurobiol Aging (2004) 25:991-999). Immunoreactivity was visualized with nickel-intensified diaminobenzidine.
A) LOAD hippocampus (neutral red counterstain) (40× objective). The arrow indicates a highly dystrophic cell with the size and morphology of a cortical pyramidal neuron, the cell type selected by laser capture for genomic analyses. Arrowheads point to one of many structures in the sections that resemble dystrophic neurites or neuropil threads.
B) LOAD hippocampus (neutral red counterstain) (40×). The arrow denotes a putative neurofibrillary tangle containing neuron. Arrowheads again indicate a dystrophic neurite. Immunohistochemistry with a rabbit polyclonal antibody directed at GAB2 residues 285-676 (Upstate Cell Signaling Solutions, Lake Placid, N.Y.) gave similar but weaker staining (not shown).
C) AD posterior cingulate gyrus (40×). Filled arrows point to relatively normal appearing, putative neurons. The open arrow points to a cell with the features of a neurofibrillary tangle bearing neuron. Immunoreactive structures clearly resembling pyramidal cell apical dendrites were also observed ascending through the cortical layers (arrowheads).
D) AD posterior cingulate cortex (100× objective). GAB2 immunoreactive cell with the flame-shaped cytoplasmic inclusion typical of the neurofibrillary tangle.

FIG. 5 shows the results of siRNA treatment. In comparison with vehicle treatment (red, upper left), in GAB2 siRNA treatment there was a 1.70-fold increase in tau phosphorylation at the Serene-262 residue (red, lower left), which is phosphorylated in LOAD neurofibrillary tangle-bearing neurons. This fold-change was not attributable to an increase in total tau (upper and lower right, green).

FIG. 6 shows gene expression data, wherein the raw expression level is shown on the y-axis and the haplotype is shown on the x-axis (right side has gene expression in samples from LOAD patients homozygous for the risk increasing GAB2 haplotype (RR) and left side has gene expression in samples from LOAD patients not homozygous for the risk increasing GAB2 haplotype (RP—heterozygous for the risk increasing and the risk decreasing (P) GAB2 haplotype; NN—homozygous for the risk non-altering GAB2 haplotype).

FIG. 8 is a table providing additional details on each SNPs 5-22 in each of the GAB2 haplotypes including location and strand.

FIG. 9 is a table providing LOAD-association significance levels and additional data of 10 SNPs located in the GRB-associated binding protein 2 (GAB2) gene on chromosome 11q14.1.

BRIEF DESCRIPTION OF THE SEQUENCES

Figure 3:
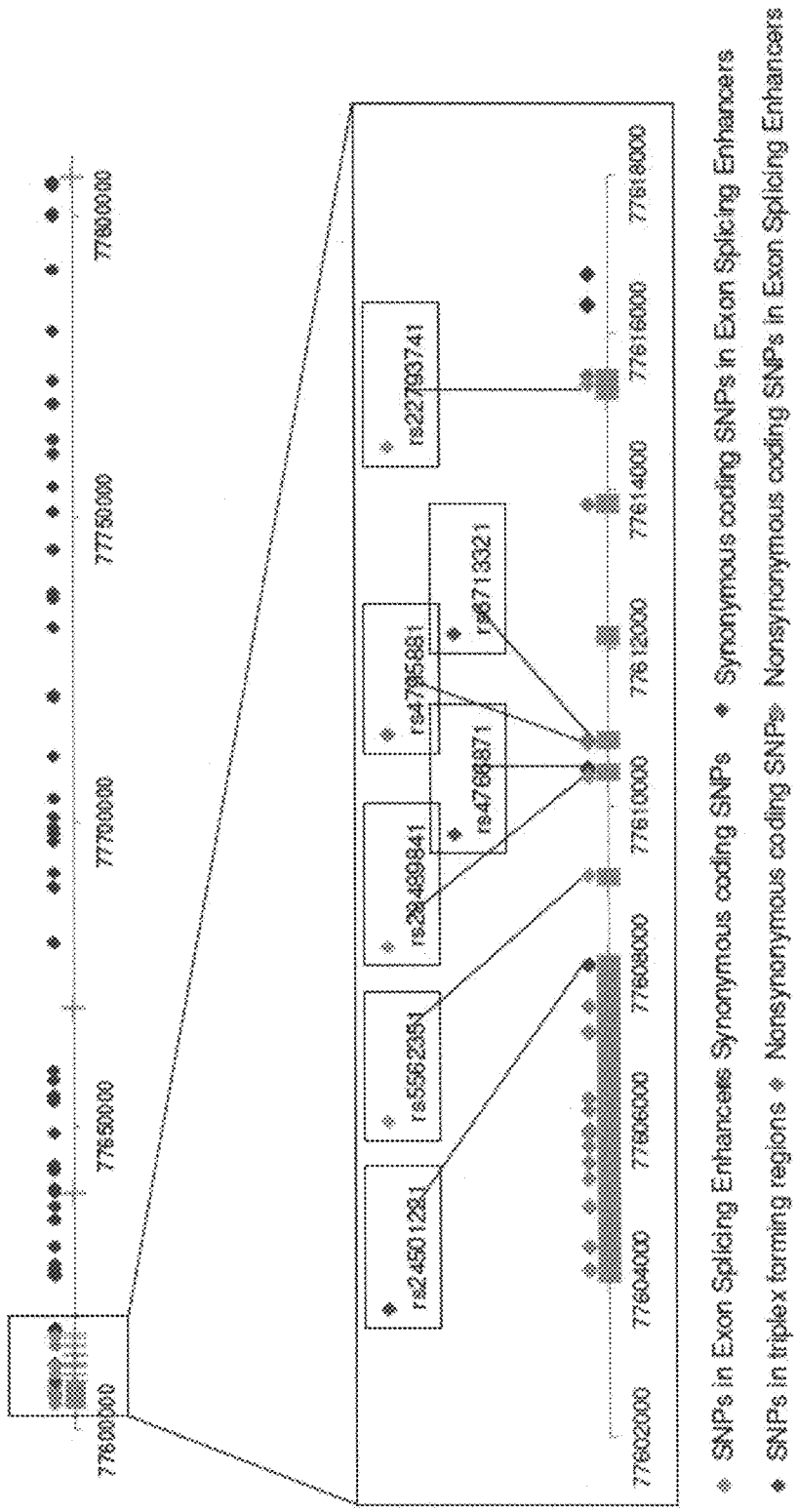

The present disclosure encompasses the following sequences with assigned sequence identifiers:

SEQ ID NO: 1—TC-GCA-TGAGGTGTCTT—Haploblock of SNPs that identify the haplotype of GAB2 that decreases LOAD risk.

SEQ ID NO: 2—CT-AAG-CAGATCAGACG—Haploblock of SNPs that identify the Haplotype of GAB2 that increases LOAD risk.

SEQ ID NO: 3—CT-AAG-CAGAGCAGCCG—Haploblock of SNPs that identify the Haplotype of GAB2 that does not alter risk for LOAD.

SEQ ID NO: 4—cDNA for GAB2 (from a fourth haplotype).

SEQ ID NO: 5—protein sequence for GAB2 (from a fourth haplotype).

GAB2-R1—cDNA sequence for LOAD risk increasing allele of human GAB2.

GAB2-R2—polypeptide sequence for LOAD risk increasing allele of human GAB2.

GAB2-P1—cDNA sequence for LOAD risk decreasing (protective) allele of human GAB2.

GAB2-P2—polypeptide sequence for LOAD risk decreasing (protective) allele of human GAB2.

GAB2-R1-Genomic—genomic sequence for LOAD risk increasing allele of human GAB2.

GAB2-P1-Genomic—genomic sequence for LOAD risk decreasing (protective) allele of human GAB2.

GAB2-Neutral-Genomic—genomic sequence for non-LOAD risk altering allele of human GAB2.

DETAILED DESCRIPTION OF THE DISCLOSURE i.) General Overview

Alzheimer's disease (AD) is a progressive neurodegenerative disorder characterized by memory and cognitive impairments and other non-cognitive behavioral symptoms. Age is the strongest risk factor, wherein almost 50% of people over the age of 85 are affected. Early-onset AD (EOAD) is associated with genetic mutations in amyloid precursor protein (APP), presenilin 1 (PSEN1) and presenilin 2 (PSEN2). However, sporadic or late-onset AD (LOAD) is multi-factorial and genetically more complex. In addition, genetic factors may account for as much as 80% of the disease risk associated with LOAD (Gatz et al. (2006) Arch. Gen. Psychiatry 63(2):168-174). While monogenic mutations cause EOAD, the only extensively validated susceptibility gene for LOAD is the apolipoprotein E (APOE-ε4) allele (Saunders et al. (1993) Neurology 43(8):1467-1472 and Farrer et al. (1997) JAMA 278(16):1349-1356). But alleles of the APOE gene do not account for all of the genetic load responsible for LOAD predisposition. Stratification by APOE-ε4 carrier status allows for the detection of association signals that are normally overwhelmed and thus, masked by the signal of APOE alleles in a non-stratified study design. Specifically, it allowed the present inventors to detect a locus that modifies the LOAD risk of individuals who carry the APOE-ε4 allele.

Late-onset Alzheimer's Disease (LOAD) is the most common age-related dementia, and is caused by neuronal death of poorly understood etiology. The most accurate method of diagnosis is the presence of characteristic plaques and tangles in the brain which can be revealed through histological examination. The apolipoprotein E (APOE-ε4) allele (supra) accounts for approximately 65% of the total risk. The disclosure encompasses a new whole-genome association analysis of single nucleotide polymorphisms (SNPs) using 502,627 SNPs in 760 histopathologically verified Alzheimer's disease (AD) cases and controls. Of the 25 SNPs with the most significant p-values in the APOE-ε4 carrier group, 10 SNPs are found to be located within the GRB2-associated binding protein 2 (GAB2) gene. There is a single haplotype block encompassing the entire gene and which contains four potentially functional non-synonymous nucleotide changes. The disclosure identifies a risk-enhancing and a risk-decreasing haplotype within the GAB2 gene. These haplotypes modify risk differentially in combination with APOE alleles. In addition, the present disclosure includes additional markers associated with increased or decreased risk of LOAD as shown in Tables 7.

ii) Definitions

The following definitions are set forth to illustrate and define the meaning and scope of the various terms used to describe the present disclosure.

The term "single polynucleotide polymorphism (SNP)" refers to a DNA sequence variation that involves a change in a single nucleotide. They present in humans with a frequency of about once in every 1000 bases and contribute to differences among individuals. The majority of SNPs have no effect. However, some affect the risk for certain diseases.

The term "haplotype" means one or more closely linked alleles, i.e., genes or DNA polymorphisms (e.g., SNPs) inherited as a unit. Different combinations of polymorphisms are known as haplotypes. The difference of a single genetic marker can delineate a distinct haplotype. Alternatively, the results from several loci could be referred to as a haplotype. For example, a haplotype can be a set of SNPs on a single chromatid that are statistically associated (i.e., inherited as a unit). It is thought that these associations, and the identification of a few alleles of a "haplotype block", can help to identify all other polymorphic sites in its region. With the identification of a haplotype block associated with a particular haplotype, one of skill in the art may readily identify all other DNA polymorphisms associated with the particular haplotype by routine sequencing of the genomic DNA of an individual having such haplotype, preferably homozygous for such haplotype. Thus, such information is valuable for investigating the genetics behind common diseases.

A "SNP haploblock identified by SEQ ID NO:" means set of at least two SNPs that are associated with an allele of a gene such as GAB2, wherein said SNPs are grouped together in form of a synthetic nucleotide sequence. The SNPs in a given haploblock may be associated with a risk increasing or risk decreasing haplotype for LOAD. Thus, when a nucleic acid is "specific to a SNP haploblock" or "specific to a SNP within a haploblock" then that nucleic acid (e.g., nucleic acid probe) is complementary to at least one SNP that is grouped within that haploblock, which may include one of the SNPs that are associated with the synthetic nucleotide sequence or any other SNP associated with the haplotype identified by the SNP haploblock. A "SNP that is specific to a SNP haploblock" is a SNP where the DNA polymorphism is found only in the particular haplotype and no other. By way of example, considering the three GAB2 haplotypes identified by the haploblocks in Table 1 below, SNP 5 is specific to the SNP haploblock identified by SEQ ID NO: 1 since the SNP haploblock identified by SEQ ID NO: 1 is the risk decreasing haplotype and this haplotype has a T at SNP 5 while the other two haplotypes have a C.

The term "HapMap" refers to a catalog of common genetic variants that occur in human beings. It describes what these variants are, where they occur in the DNA, and how they are distributed among individuals within populations and among populations in different parts of the world (A haplotype map of the human genome (2005) *Nature* 437:1299-1320).

iii.) Haplotypes of GAB2 As Genetic Markers for AD

The genetic sequences of different individuals are remarkably similar. When the chromosomes of two humans are compared, their DNA sequences can be identical for hundreds of bases. But at about one in every 1000 to 1,200 bases, on average, the sequences will differ. As such, one individual might have an A at that location, while another individual has a G, or a person might have extra bases at a given location or a missing segment of DNA. Differences in individual bases are the most common type of genetic variation. These genetic differences are known as single nucleotide polymorphisms (SNPs) (supra). SNPs act as markers to locate genes in DNA. Given the relatively close spacing between these SNPs, SNPs are typically inherited in blocks.

GAB2 is scaffolding protein involved in multiple signaling pathways that impact AD pathology (see FIG. 2). GAB2 acts downstream of growth factor and cytokine receptors and is the primary activator of the phosphatidylinositol 3-kinase (PI3K) signaling pathway. PI3K activates Akt, which in turn inhibits Gsk3, which has been shown to inhibit phosphorylation of Tau. Activated Akt also inhibits Bad and the FOXO family proteins, both of which cause neuron death. Inhibition of PI3K signaling decreases the efficacy of the Acetylcholinesterase inhibitors donepezil and galanthamine (i.e., treatments for AD) which act, at least in part, through a pathway whose main activator is GAB2. Furthermore, Gab2 associates with Grb2 and Sos which then activate the Erk ½ signaling cascade. The Erk signaling cascade influences learning and memory through Creb. In addition, GAB2 plays a role in mast cell degranualtion through FCεRI signaling. GAB2 complexes with Fyn to initiate a degranulation cascade through Pkc. For example, GAB2 knockout mice are viable, but show profound mast cell deficiencies and reduced degranulation.

Despite the postulation of many genes as possible susceptibility factors in LOAD, the only well-established genetic link is the APOE-ε4 allele. Association studies traditionally fail to replicate due to underlying genetic structure, low sample number, poor genomic coverage and incorrect diagnosis. However, the inventors have addressed these issues by controlling for underlying genetic structure and interrogating 502,627 SNPs in 1469 samples of which 1086 samples are histopathologically confirmed based on the presence or absence of plaques and tangles in the postmortem samples. The inventors have further enhanced the analysis of this complex disorder by stratifying the data for APOE-ε4 carrier status in order to detect signals that would normally be masked in a non-stratified design. Thus, the disclosure identifies two GAB2 haplotype blocks wherein one is associated with increased risk for LOAD (SEQ ID NO: 1) and the other is associated with decreased risk for LOAD (SEQ ID NO: 2), wherein the latter exhibits a strong protective effect. These haplotypes modify risk differentially in combination with APOE alleles.

Figure 1:
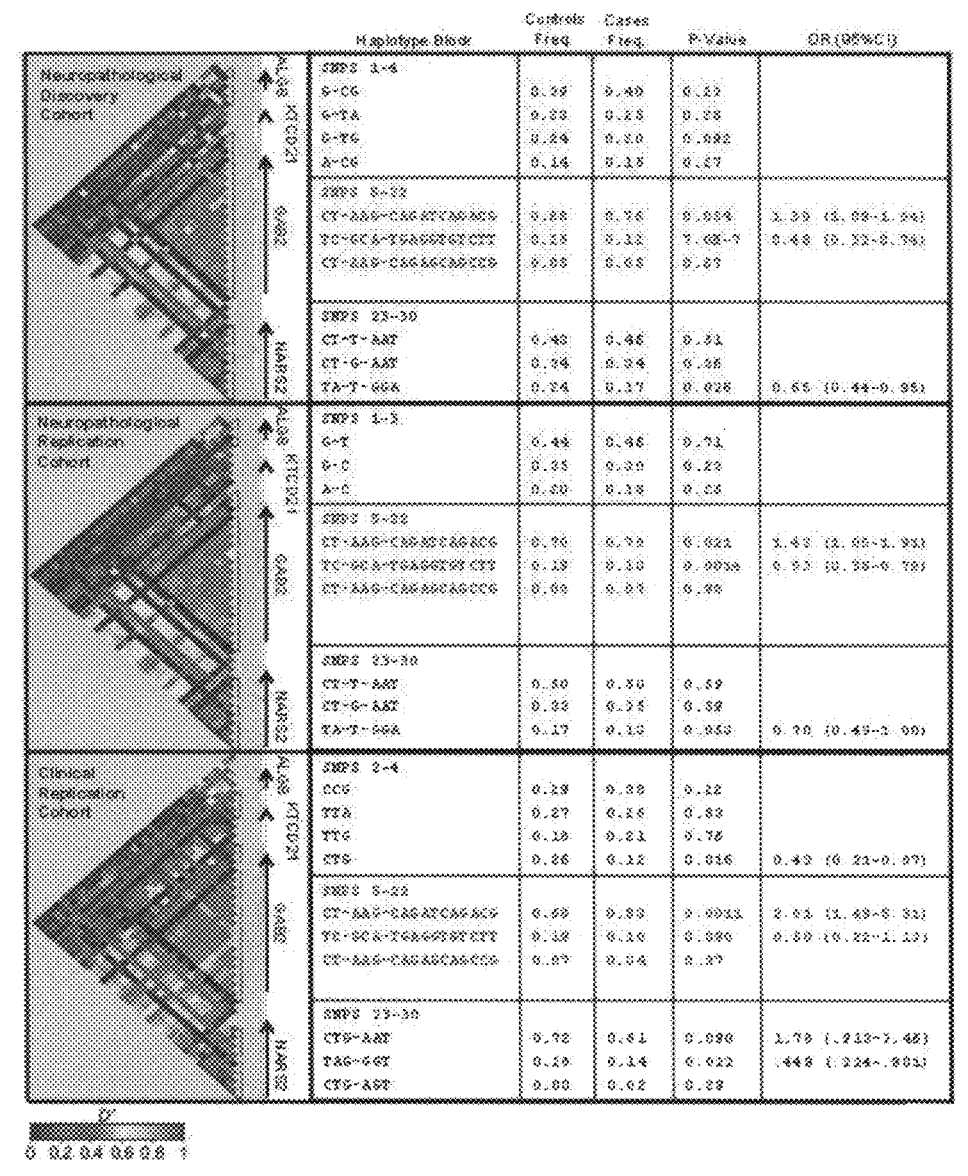

There is a single haplotype block encompassing the entire GAB2 gene and which contains four potentially functional non-synonymous nucleotide changes. The haplotype block is shown in FIG. 1. SNPS 5-22 are depicted horizontally within the haploblock as shown in Table 1 below.

TABLE 1

| SNPs 5-22 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|
| Risk Increasing Haplotype | C | T | — | A | A | G | — | C | A | G | A | T | C | A | G | A | C | G |
| Risk Decreasing Haplotype | T | C | — | G | C | A | — | T | G | A | G | G | T | G | T | C | T | T |
| Other Haplotype* | C | T | — | A | A | G | — | C | A | G | A | G | C | A | G | C | C | G |

*Does not increase or decrease risk.
As shown in Table 1, SNPS 7 and 11 were insignificant while all others are considered significant. The four potentially functional non-synonymous nucleotide changes are believed to be among the significant SNPS within this haplotype. As depicted, the risk-increasing and risk-decreasing haplotype are within the GAB2 gene. These haplotypes modify risk differentially in combination with APOE alleles.

Determining the functional variant in the GAB2 haplotype block is challenging because the block spans 189 kb and includes at least 614 known SNPs, each of which reflects a significant association with AD due to the significant haplotype block. Of the 614 described SNPs, 4 are non-synonymous and are the best candidates for causing the disease risk-modifying effects of the haplotype. It is unlikely that a complex, partially penetrant disease like LOAD would have a truncated protein or other catastrophic risk or protective allele. However, it is likely that subtle genetic differences lead to altered protein expression or phosphorylation. PupaSNP is used to identify known SNPs that are likely to play a significant physiological role due to their location in exonic splicing enhancers (ESEs) or triplex forming regions (TRPs), both of which provide for sequence specific regulation of expression and splicing (see FIG. 3). The present disclosure encompasses a high density whole genome association study of LOAD, utilizing a large set of highly accurate clinically and pathologically characterized samples. Notably, replication of six SNPs in three independent study populations reveal a haplotype block encompassing GAB2 on chromosome 11q14.1 that is protective against LOAD in APOE-ε4 carriers. This finding is significant since GAB2 is integral to pathways affecting Tau phosphorylation, Creb activation, mast cell degranulation, and APOE protein synthesis.

An array platform (e.g., AFFYMETRIX 500K array) can be used to genotype all three populations that are utilized. However, any other platform can be employed as well. There are two reasons for confidence that the genotype calls are correct and that the association effect observed is indeed accurate (and not due to a bias of any single platform used). First, the observation is not a single SNP association, but rather the association of a large haplotype block which is in agreement with the LD structure of the HapMap CEPH population. Second, one benefit of using SNiPer-HD for genotype calls is the generation of a quality score measuring how well the clustering algorithm is able to separate the chip output into three distinct Gaussians. All six SNPs showing replication in the region have high quality scores (>0.45), indicating that the data for each SNP clustered into three distinct Gaussians corresponding to the three possible genotype calls.

The whole genome association study uses an evenly distributed panel of SNPs across the genome with an average inter-marker distance of 6 kb in a sample of 1469 well characterized AD cases and age-matched unaffected controls. As such, it identified risk-modifying haplotypes of GAB2 for APOE-ϵ4 carriers. Ultra-high density SNP genotyping is successfully employed to identify risk and protective loci in complex diseases because it is rigorously controlled and performed using a sufficiently reliable and dense set of markers. Further efforts are in progress to identify the functional variant(s) present in GAB2 in order to include pre-symptomatic risk assessment strategies and actual drug targets.

Several additional markers were identified in or near other genes that have utility in diagnosing and monitoring late onset Alzheimer's disease which may be used alone or in combination with the markers disclosed herein or otherwise known in the art such as the APOE-ϵ4 allele.

iv.) Methods of Diagnosing AD

The disclosure provides a method of assigning a subject to a late onset Alzheimer's disease (LOAD) risk group in order to assess the likelihood of the subject being afflicted with the disease. This method can be employed to assess the risk at early stages of disease progression. The method includes providing a biological sample from the subject, detecting a marker in a biological sample, which can be a haplotype of GAB2 associated with LOAD or any of the markers on Table 7, and assigning the subject to the late onset Alzheimer's disease (LOAD) risk group based upon the presence or absence of the haplotype. The method involves directly or indirectly detecting the presence or absence of the markers. For example, the haplotype of GAB2 may be associated with increased risk of LOAD and the subject is then assigned to a high LOAD risk group if the subject has the haplotype of GAB2. As an example of such is the haplotype of GAB2 identified by the SNP haploblock identified by SEQ ID NO: 2. Thus, the presence of haploblock identified by SEQ ID NO: 2 indicates that the subject is at increased risk for developing the disease. Alternatively, the marker may be associated with decreased risk of LOAD and the subject is assigned to a low LOAD risk group if the subject has the marker. An example of such is the haplotype of GAB2 identified by the SNP haploblock identified by SEQ ID NO: 1. Thus, the presence of haploblock identified by SEQ ID NO: 1 indicates that the subject is at a decreased risk for developing the disease. In addition, the subject may be further stratified by LOAD risk group based upon whether the subject carries an apolipoprotein E allele associated with increased or altered LOAD risk. By way of example, APOE-ϵ4, is commonly associated with LOAD. In addition, various haplotypes of APOE have been associated with LOAD risk groups as set forth in U.S. patent Publ. 2005/0277129. Finally multiple markers disclosed herein may be used in combination to improve the accuracy, preferably two or more, three or more, four or more, five or more, or ten or more of the markers may be used.

The disclosure contemplates that the markers may be detected by a variety of methodologies or procedures that are well know in the art including, but not limited to, nucleic acid hybridization, antibody binding, activity assay, polymerase chain reaction (PCR), S1 nuclease assay and via gene chip or microarray as well as any other assay known in the art that may be used to detect the SNPs associated with a haplotype or the gene product produced from the gene of the haplotype including mRNA and protein. For example, the haplotype of GAB2 can be detected by nucleic acid hybridization using at least one hybridization probe specific to a SNP specific to the SNP haploblock identified by SEQ ID NO: 1 or SEQ ID NO: 2 (see FIG. 1 for SNPS 5-22). Hybridization of a SNP-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. SNP-specific oligonucleotides may be synthesized directly on the solid support or attached to the solid support subsequent to synthesis. Solid-supports suitable for use in detection methods of the disclosure include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the SNP-specific oligonucleotide or target nucleic acid. Detecting the nucleotide or nucleotide pair of interest may also be determined using a mismatch detection technique, including but not limited to the RNase protection method using riboprobes (Winter et al. (1985) *Proc. Natl. Acad. Sci. USA* 82:7575; Meyers et al. (1985) Science 230:1242) and proteins which recognize nucleotide mismatches, such as the *E. coli* mutS protein (Modrich (1991) *Ann. Rev. Genet.* 25:229-53). Alternatively, variant SNPs or variant alleles can be identified by single strand conformation polymorphism (SSCP) analysis (Orita et al. (1989) *Genomics* 5:874-9); Humphries et al. (1996) in MOLECULAR DIAGNOSIS OF GENETIC DISEASES, Elles, ed., pp. 321-340) or denaturing gradient gel electrophoresis (DGGE) (Wartell et al. (1990) *Nucl. Acids Res.* 18:2699-706); Sheffield et al. (1989) *Proc. Natl. Acad. Sci. USA* 86:232-6). A polymerase-mediated primer extension method may also be used to identify the polymorphism(s). Several such methods have been described in the patent and scientific literature and include the "Genetic Bit Analysis" method (WO 92/15712) and the ligase/polymerase mediated genetic bit analysis (U.S. Pat. No. 5,679,524. Related methods are disclosed in WO 91/02087, WO 90/09455, WO 95/17676, and U.S. Pat. Nos. 5,302,509 and 5,945,283. Extended primers containing the complement of the polymorphism may be detected by mass spectrometry as described in U.S. Pat. No. 5,605,798. Another primer extension method is allele-specific PCR (Ruano et al. (1989) *Nucl. Acids Res.* 17:8392; Ruano et al. (1991) *Nucl. Acids Res.* 19:6877-82); WO 93/22456; Turki et al. (1995) *J. Clin. Invest.* 95:1635-41). The haplotype for a gene of an individual may also be determined by hybridization of a nucleic acid sample containing one or both copies of the gene, mRNA, cDNA or fragment(s) thereof, to nucleic acid arrays and subarrays such as described in WO 95/112995. The arrays would contain a battery of SNP-specific or allele-specific oligonucleotides representing each of the polymorphic sites to be included in the haplotype.

The step of detecting the presence or absence of a marker disclosed herein or a close isoform thereof may be carried out either directly or indirectly by any suitable means. A variety of techniques are known to those skilled in the art (supra). All generally involve the step of collecting a biological sample containing DNA or protein from the subject, and then detecting whether or not the subject possesses the marker or a close isoform thereof. For example, the detecting step may be carried out by collecting a biological sample from the subject (any fluid or tissue containing the markers associated with the haplotype), and then determining the presence or absence of the haplotype in the sample (e.g., by nucleic acid hybridization, immunoassay such as antibody binding, activity assay, polymerase chain reaction (PCR), S1 nuclease assay, via gene chip or microarray, via isoelectric focusing, etc.). Other markers may also be used that are associated with the markers disclosed herein such as SNPs or other polymorphic markers that are in close enough proximity to have a statistically significant association with the marker disclosed herein (i.e., other markers in linkage disequilibrium with a marker disclosed herein). It will be readily appreciated by those of skill in the art that the detecting steps described herein may be carried out directly or indirectly. Thus, for example, if a marker or a close isoform thereof is detected in the subject, then it is determined that the subject is either at increased or decreased risk for LOAD depending on which marker or close isoform thereof is identified (i.e., a significant enough number of markers associated with a haplotype). If, for example, the subject is identified to carry the risk increasing GAB2 haplotype in combination with the APOE-ε4 allele then the subject is very likely to be at increased risk of developing LOAD. If, for example, the subject is identified to carry the risk decreasing GAB2 haplotype in combination with the APOE-ε4 allele then the subject is very likely not at increased risk of developing LOAD or even at a lower risk of developing LOAD compared to APOE-ε4 carriers that do not carry any GAB2 haplotype associated with either SEQ ID NO: 1 or SEQ ID NO: 2. Other means of indirectly determining a risk for LOAD could be by measuring other polymorphic markers that are in statistically significant proximity to any of the SNPs of the GAB2 haplotypes.

The disclosure also provides set of molecular probes for detection, including at least two probes capable of detecting, directly or indirectly, a marker disclosed herein associated with increased or decreased risk of LOAD, wherein the molecular probes are not associated with a microarray of greater than 1000 elements, a microarray with greater than 500 elements, a microarray with greater than 100 elements a microarray with greater than 50 elements, or are not associated with a microarray. In preferred embodiments, at least one of the probes is capable of detecting, directly or indirectly, a marker disclosed herein associated with increased risk of LOAD and at least one other probe is capable of detecting, directly or indirectly, a marker disclosed herein associated with decreased risk of LOAD. Thus, the probes are able to detect directly or indirectly the presence or absence of such marker disclosed herein.

Detecting the presence or absence of a marker disclosed herein or a close isoform thereof may be carried out either directly or indirectly. For example, SNP testing technologies can be employed to detect the haplotype of GAB2. Based upon a patient's specific genotype (SNP pattern) an estimate of the patient's relative risk for LOAD could be provided. This would include genotyping first for ApoE 2/3/4 status, and then further genotyping for the GAB2 haplotype status. This includes Odds Ratio estimates based on carrier status of these two genes.

Detection of the disease also includes detection of the haplotype by any SNPs/markers within the haplotype, but also indirectly through SNPs/markers outside the haplotype and leveraging linkage disequilibrium to identify carriers of the haplotype.

In addition to determining a patient's relative risk for LOAD, the diagnosis may include prescribing therapeutic regimens to treat, prevent or delay onset of LOAD.

In certain preferred embodiments, the method of diagnosis will further include direct or indirect detection of APOE alleles associated with LOAD, preferably the APOE-ε4 allele. Such detection may be performed using any of the detection methods available to one of skill in the art and the markers disclosed herein and APOE alleles may be detected using the same or different methods and may be detected at the same or different times. Further, the method of diagnosis may rely upon the information regarding the APOE alleles of the subject that had been previously determined. With information regarding the marker disclosed herein and APOE alleles of a subject, the diagnosis of risk may be determined and present in the form of Odds Ratio estimates for the set of alleles the subject has.

v.) Screening Methods

The disclosure also provides a method for screening for a therapeutic agent effective to inhibit development of cell deterioration associated with dementia. This method includes incubating neuronal cells in vitro with an agent to be tested, measuring PI3K activity, comparing the activity to PI3K activity in the absence of the agent to be tested, and identifying the therapeutic agent by indication of PI3K activity in the presence of the agent. The therapeutic agent can inhibit the cell deterioration associated with dementia such as LOAD. These methods also includes incubating neuronal cells in vitro with an agent to be tested, measuring GAB2 activity directly or indirectly, comparing the activity to GAB2 activity in the absence of the agent to be tested, and identifying the therapeutic agent by detection of modulation of GAB2 activity in the presence of the agent. Examples of measuring GAB2 activity include measuring mRNA level, mRNA transcription rate, protein level, assaying the activity of the GAB2 protein or one of the proteins that it regulates such as PI3K, and measuring activity of a reporter gene operably linked to a GAB2 regulatory element which can include the GAB2 promoter and/or one or more GAB2 enhancer or repressor elements. The therapeutic agent can inhibit the cell deterioration associated with dementia such as LOAD. Thus, the therapeutic agent will act as an agonist to activate PI3K. For the purpose of screening for such agents, the disclosure also includes a non-human transgenic animal or mammalian cell based assay (preferably a human cell based assay) with a genome including the human GAB2 gene associated with the haplotype identified by the SNP haploblock of SEQ ID NO: 1 or SEQ ID NO: 2. The non-human animal or mammalian cell based assay can be used as a disease model for screening therapeutic compounds for treatment of LOAD. Thus, the disclosure provides a method for screening for a therapeutic agent effective to inhibit development of cell deterioration associated with dementia, wherein the method includes providing a transgenic animal or mammalian cell based assay with a genome including the human GAB2 gene associated with the haplotype identified by the SNP haploblock of SEQ ID NO: 1 or SEQ ID NO: 2. The method further includes administering to the transgenic animal an agent to be tested for its effectiveness in treating or preventing the cell deterioration associated with dementia, and assessing the effectiveness of the agent.

vi.) Therapeutic Methods and Formulations

In people with AD, changes in the brain may begin 10 to 20 years before any visible signs or symptoms appear. Some regions of the brain may begin to shrink, resulting in memory loss, the first visible sign of AD. Over time, AD progresses through three main stages: mild, moderate, and severe. These stages are characterized by a collection of signs and symptoms and behaviors that individuals with AD experience. People with mild symptoms of AD often seem healthy, but they are actually having difficulty making sense of the world around them. Initial symptoms are often confused with changes that take place in normal aging. Symptoms and early signs of AD may include difficulty learning and remembering new information, difficulty managing finances planning meals, taking medication on schedule, depression symptoms (sadness, decreased interest in usual activities, loss of energy), getting lost in familiar places, etc. In moderate AD, the damaging processes occurring in the brain worsen and spread to other areas that control language, reasoning, sensory processing, and thought. In this stage, symptoms and signs of AD become more pronounced and behavioral problems may become more obvious. Signs and symptoms of moderate AD may include forgetting old facts, repeating stories and/or questions over and over, making up stories to fill gaps, difficulty performing tasks, following written notes, agitation, restlessness, repetitive movements, wandering, paranoia, delusions, hallucinations, deficits in intellect and reasoning, lack of concern for appearance, hygiene, and sleep, etc. In the advanced stage of AD, damage to the brain's nerve cells is widespread. At this point, full-time care is typically required. People with severe AD may have difficulty walking, and they often suffer complications from other illnesses, such as pneumonia. Signs of severe AD may include screaming, mumbling, speaking gibberish, refusing to eat, failing to recognize family or faces, and difficulty with all essential activities of daily living.

The disclosure provides a method of decreasing or preventing neuronal cell deterioration in a subject at risk for LOAD, wherein the method includes administering a compound that mimics the function of GAB2. By way of example, such a compound may modulate PI3K or ERK activity. Such a compound is provided by the instant disclosure and is encoded by the amino acid sequence of SEQ ID NO: 5. The corresponding nucleic acid sequence is encoded by SEQ ID NO: 4. Additional compounds and agents may be readily identified by the screening methods discussed above. Such modulating may include, for example, turning on PI3K activity which will in turn activate the protein AKT which will lead to inhibition of TAU which is associated with increased neurofibrillary tangles and plaques in the brain that are characteristic of LOAD, and to inhibition of the FOXO proteins and BAD protein which increase cell death. Since PI3K is a known cancer-related gene, many compounds that modulate PI3K activity have been identified and either may be used directly in the methods herein or may be used to design libraries for further screening of PI3K modulators. Examples of such PI3K modulators may be found in U.S. Patent Application Nos: 2006005832, 20060128732, 20060106038, and 20020151549. Such modulating may also include, for example, turning on the ERK 1 and 2 cascades will lead to activated CREB which enhances learning and memory. Thus, a compound that mimics GAB2 can be used as a therapeutic agent or agonist that is expected to decrease or prevent neuronal cell deterioration associated with LOAD.

GAB2 agonists, mimics, and modulatory agents (e.g., drugs based on SEQ ID NO: 5) are formulated as pharmaceuticals to be used in the methods of the disclosure such as for the treatment and prevention of AD, particularly LOAD. Any composition or compound that can stimulate a biological response associated with the binding of a ligand analogue (i.e., an agonist or modulator) to GAB2 or that can mimic GAB2 can be used as a pharmaceutical in the disclosure. General details on techniques for formulation and administration are well described in the scientific literature (see "Remington's Pharmaceutical Sciences", Maack Publishing Co, Easton Pa.). GAB2 agonist, mimic, and modulatory agent pharmaceutical formulations can be prepared according to any method known in the art for the manufacture of pharmaceuticals. The GAB2 agonists, mimics, and modulatory agents used in the methods of the disclosure can be formulated for administration in any conventionally acceptable way including via intravenous injection, IM, IP, orally, topically, vaginally or rectally. Oral administration is preferred. Illustrative examples are set forth below.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, capsules, liquids, lozenges, gels, syrups, slurries, suspensions, etc., suitable for ingestion by the patient. Pharmaceutical preparations for oral use can be obtained through combination of GAB2 agonist compounds with a solid excipient, optionally grinding a resulting mixture, and processing the mixture of granules, after adding suitable additional compounds, if desired, to obtain tablets or pills. Suitable solid excipients are carbohydrate or protein fillers which include, but are not limited to, sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate. Pharmaceutical preparations of the disclosure that can also be used orally are, for example, push-fit capsules made of gelatin, as well as soft, sealed capsules made of gelatin and a coating such as glycerol or sorbitol. Push-fit capsules can contain GAB2 agonists, mimics, and modulatory agents mixed with a filler or binders such as lactose or starches, lubricants such as talc or magnesium stearate, and, optionally, stabilizers. In soft capsules, the GAB2 agonist, mimic, and modulatory agent compounds may be dissolved or suspended in suitable liquids, such as fatty oils, liquid paraffin, or liquid polyethylene glycol with or without stabilizers.

Aqueous suspensions of the disclosure contain a GAB2 agonist, mimic, and modulatory agent in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol monooleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending a GAB2 agonist, mimic, and modulatory agent in a vegetable oil, such as arachis oil, olive oil, sesame oil or coconut oil, or in a mineral oil such as liquid paraffin. The oil suspensions can contain a thickening agent, such as beeswax, hard paraffin or acetyl alcohol. Sweetening agents can be added to provide a palatable oral preparation. These formulations can be preserved by the addition of an antioxidant such as ascorbic acid.

Dispersible powders and granules of the disclosure suitable for preparation of an aqueous suspension by the addition of water can be formulated from a GAB2 agonist, mimic, and modulatory agent in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, can also be present.

The pharmaceutical formulations of the disclosure can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

When the drugs are delivered by intravenous injection, the GAB2 agonist, mimic, and modulatory agent pharmaceutical formulations of the disclosure can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

vii.) Administration and Dosing Regimen of GAB2 Agonists, Mimics, and Modulatory Agents The GAB2 agonists, mimics, and modulatory agents used in the methods of the disclosure can be administered in any conventionally acceptable way including via intravenous injection, IM, IP, orally, topically, vaginally or rectally. Oral administration is preferred. Administration will vary with the pharmacokinetics and other properties of the drugs and the patients' condition of health. The methods of the disclosure reduce cellular deterioration in patients who suffer from LOAD. The amount of GAB2 agonist, mimic, and modulatory agent that is adequate to accomplish this is considered the therapeutically effective dose. Precise dose schedules cannot be stated. The dosage schedule and amounts effective for this use, i.e., the "dosing regimen," will depend upon a variety of factors, including the stage of LOAD, the severity of LOAD, the severity of the adverse side effects, the general state of the patient's health, the patient's physical status, age and the like. In calculating the dosage regimen for a patient, the mode of administration is also taken into consideration. The dosage regimen must also take into consideration the pharmacokinetics, i.e., the agonist, mimic, and modulatory agent rate of absorption, bioavailability, metabolism, clearance, and the like.

The state of the art allows the clinician to determine the dosage regimen for each individual patient who suffers from LOAD (mild, moderate and severe stages). The formulations should provide a sufficient quantity of GAB2 agonist, mimic, and modulatory agent to effectively ameliorate LOAD which is characterized by symptoms such as memory loss, depression, restlessness, etc. A typical pharmaceutical formulation for oral administration of GAB2 agonist, mimic, and modulatory agent would depend on the stage of LOAD and condition of the patient. For example, a GAB2 agonist, mimic, and modulatory agent may be administered to a patient through mono therapy (i.e., with no other Alzheimer's medications) or in combination therapy with other Alzheimer's drugs including cholinesterase inhibitors such as DONEPEZIL (Aricept), GALANTAMINE (Razadyne), RIVASTIGMINE (Exelon), and TACRINE (Cognex), drugs that generally used for treatment of mild to moderate AD. NAMENDA (memantine HCl), a drug used for treatment of moderate to severe AD may also be used in combination with GAB2 agonists, mimics, and modulatory agents. Thus, the dosages of selective GAB2 agonists, mimics, and modulatory agents administered to a patient may vary depending on age, degree of illness, drug tolerance, and concomitant medications and conditions.

viii.) Examples

The following specific examples are intended to illustrate the disclosure and should not be construed as limiting the scope of the claims.

In $\epsilon4$ carriers from neuropathologically verified discovery, neuropathologically verified replication, and clinically characterized replication cohorts of 1425 cases and controls, LOAD was associated with six SNPs from the GRB-associated binding protein 2 (GAB2) gene and with a common haplotype encompassing the entire GAB2 gene. Of those homozygous for both the $\epsilon4$ allele and the GAB2 risk haplotype, 98.7% had LOAD. In addition, the GAB2 gene was over-expressed in pathologically vulnerable neurons, the GAB2 protein was detected in neurons, tangle-bearing neurons and dystrophic neurites, and interference with GAB2 gene expression increased Tau phosphorylation. Collectively, the inventors have shown that GAB2 modifies LOAD risk in APOE $\epsilon4$ carriers and influences Alzheimer's neuropathology.

More specifically, whole-genome association analysis of single nucleotide polymorphisms (SNPs) was performed using 502,627 SNPs in 760 histopathologically verified AD cases and controls (discovery cohort). All samples were stratified for APOE-$\epsilon4$ carrier status prior to analysis to identify additional LOAD risk loci. Of the 25 SNPs with the most significant p-values in the APOE-$\epsilon4$ carrier group, 10 were located within the GRB2-associated binding protein 2 (GAB2) gene (p-valmax=$5.9 \times 10^{-7}$; OR=0.2571 (0.1173-0.5636). These results were replicated in an additional 326 histopathologically diagnosed cases and controls, also stratified for APOE-$\epsilon4$ carrier status (replication cohort 1). An additional cohort of 383 clinically diagnosed LOAD samples provided further validation for the GAB2 association (replication cohort 2). There is a single haplotype block encompassing the entire gene and which contains four potentially functional non-synonymous nucleotide changes. This analysis identified a risk-enhancing and a risk-decreasing haplotype within the GAB2 gene which modify risk differentially in combination with APOE alleles in LOAD.

Thus, the inventors conducted individualized genome-wide surveys of 502,627 single nucleotide polymorphisms (SNPs) in an effort to characterize and confirm novel LOAD susceptibility genes in three separate cohorts of LOAD cases and controls, including a discovery cohort of clinically and neuropathologically characterized expired brain donors, a replication cohort of similarly characterized expired brain donors, and a replication cohort of clinically characterized living subjects. The expired brain donor cohorts were selected to exclude clinically misdiagnosed cases and cognitively normal but neuropathologically affected elderly controls; the clinical cohort was selected to confirm genetic associations independent of any brain donor selection bias. Within each cohort, LOAD cases and controls were stratified into subgroups of APOE ε4 carriers and non-carriers, permitting the investigation of genes that modify LOAD risk in the ε4 carriers and genes that might otherwise be masked by disproportionately large ε4 effects in the non-carriers. The inventors discovered associations between a common gene and LOAD in APOE ε4 carriers in the three neuropathological and clinical cohorts and showed that the implicated gene is associated with AD neuropathology in neuronal microarray and immunohistochemical studies. Further provided is a possible mechanism by which GAB2 modifies AD risk in a preliminary small-interfering RNA (siRNA) study.

Example 1

Design

The software program STRUCTURE (Pritchard et al. (2000) *Genetics* 155:945-59) was used to test for underlying genetic stratification, using 5000 randomly selected SNPs with at least 100 SNPs per chromosome. Initial analysis yielded empirical evidence of three populations (K=3). One, which contained fourteen samples and was far removed from the rest of the study population, was eliminated from further analyses. STRUCTURE was re-run with K=2, and each sample was assigned an admixture of the resulting populations. Comparison of the resulting case and control populations defined by these admixture vectors yielded a silhouette score of 0.06, indicating that while the samples in this study are the likely result of admixture of two populations, the distribution of those populations is equivalent in cases and controls (Pritchard et al. (2000) *Genetics* 155(2):945-59).

Example 2

Introduction to High-Density Genome-Wide Association Study

The genome-wide association study was performed using 502,627 SNPs on DNA samples extracted from brain tissue or blood of donors who were at least 65 years of age at the time of their death. The donors included a postmortem cohort of 664 patients who satisfied clinical and neuropathological criteria for the diagnosis of AD and 422 persons that did not meet clinical or neuropathological criteria for AD as controls (broken up into a 70% "discovery cohort" and a 30% "replication cohort 1" design). Tissue and neuropathological diagnoses were supplied by investigators from twenty National Institute on Aging Alzheimer's Disease Centers (ADCs) in accordance with an agreement with these Centers, the National Institute on Aging, and the National Alzheimer's Coordinating Center (NACC). Additional post-mortem samples were received from Sun Health Research Institute and the Netherlands Brain Bank. An additional sample series including 228 clinically-assessed antemortem AD patients and 155 clinically assessed antemortem controls ("replication cohort 2") was provided by the Mayo Clinic Rochester. APOE genotypes were obtained by either pyrosequencing (Ahmadian et al. (2000) *Anal. Biochem.* 280(1):103-110) or restriction fragment length polymorphism (RFLP) analysis (Lai et al. (1998) *Genomics* 54(1):31-38).

A three-tiered approach was used for the analysis of the genome-wide association study. The postmortem set was split into two cohorts matched for sex and age, a discovery cohort containing 70% of the postmortem sample ("discovery cohort") and a replication cohort containing 30% of the postmortem samples ("replication cohort 1"). An ante-mortem series from the Mayo Clinic Rochester was used as a second replication cohort ("replication cohort 2"). SNiPer-HD (Hua et al. (2007) *Bioinformatics* 23(1):57-63) and BRLMM were used to call the genotypes and the results were filtered to exclude any SNPs with SNiPer-HD quality score less than 0.45 (excludes monomorphic loci, and loci that do not cluster into three distinct Gaussians), those with Hardy Weinberg equilibrium p-value less than 0.01 or minor allele frequency less than 3%, and those where concordance between SNiPer-HD calls and BRLMM calls is less than 98%. After filtering, 321,953 SNPs remained. Allelic chi squares were computed for each SNP in the discovery cohort (70%) in 3 classes: all samples, APOE-ε4 carriers and APOE-ε4 non-carriers.

There were no loci in the ApoE-ε4 non-carriers that had a significant p-value after Bonnferroni correction for multiple testing (321,953 independent tests). Only one SNP, rs4420638, the only SNP on the AFFYMETRIX 500K Mapping Array in linkage disequilibrium (LD) with the ApoE-ε4 locus, was significant in the entire sample after multiple testing correction. Two SNPs in the ApoE-ε4 carrier population were significant after Bonferroni multiple testing correction. One of these SNPs, rs2373115, is located in an intron of GRB2-associated binding protein 2 (GAB2). Visual inspection revealed that ten of the top twenty-five SNPs in the ApoE-ε4 carriers stratified analysis were located in the introns or coding sequence of GAB2. These ten SNPs were then interrogated in the 30% replication cohort and the Mayo Clinic Jacksonville replication cohort (see Table 2 below). All ten SNPs examined were significant (p-value<0.05) in the 30% cohort, and six SNPs were significant in the Mayo Rochester ante-mortem cohort. The most significant p-values and lowest odds ratios (indicating a protective allele) were found to be located toward the distal, 5' end of GAB2 (see Table 2 below).

TABLE 2

| Rank | SNP | dbsnp RS ID | Position | Gene | Gene Relationship | P-Value | OR (95% CI) |
|---|---|---|---|---|---|---|---|
| DISCOVERY COHORT | | | | | | | |
| 10 | SNP_A-2208459 | rs901104 | 77608147 | GAB2 | intron | 1.11E−05 | 0.4036 (0.2277-0.7153) |
| 3 | SNP_A-4215188 | rs1385600 | 77613814 | GAB2 | CDS--synonymous | 2.10E−06 | 0.2805 (0.127-0.6194) |
| 7 | SNP_A-2012248 | rs1007837 | 77618724 | GAB2 | intron | 3.84E−06 | 0.3793 (0.2163-0.6651) |
| 16 | SNP_A-1882998 | rs2510038 | 77643682 | GAB2 | intron | 8.92E−05 | 0.4094 (0.2293-0.731) |
| 8 | SNP_A-1841568 | rs4945261 | 77667908 | GAB2 | intron | 8.00E−06 | 0.2844 (0.1263-0.6404) |

TABLE 2-continued

| Rank | SNP | dbsnp RS ID | Position | Gene | Gene Relationship | P-Value | OR (95% CI) |
|---|---|---|---|---|---|---|---|
| 12 | SNP_A-1826565 | rs7101429 | 77670615 | GAB2 | intron | 4.62E-05 | 0.4703 (0.2666-0.8297) |
| 23 | SNP_A-2112731 | rs10793294 | 77674051 | GAB2 | intron | 0.0002368 | 0.381 (0.1898-0.7651) |
| 5 | SNP_A-2153680 | rs4291702 | 77678896 | GAB2 | intron | 2.96E-06 | 0.3925 (0.2245-0.6862) |
| 4 | SNP_A-2313615 | rs7115850 | 77722719 | GAB2 | intron | 2.30E-06 | 0.2764 (0.1273-0.5998) |
| 2 | SNP_A-2012255 | rs2373115 | 77768798 | GAB2 | intron | 5.90E-07 | 0.2571 (0.1173-0.5636) |
| | | | | | REPLICATION 1 COHORT | | |
| 10 | SNP_A-2208459 | rs901104 | 77608147 | GAB2 | intron | 0.04519 | 1.068 (0.27-4.19) |
| 3 | SNP_A-4215188 | rs1385600 | 77613814 | GAB2 | CDS--synonymous | 0.01321 | 0.36 (0.061-2.12) |
| 7 | SNP_A-2012248 | rs1007837 | 77618724 | GAB2 | intron | 0.03199 | 1.068 (0.27-4.19) |
| 16 | SNP_A-1882998 | rs2510038 | 77643682 | GAB2 | intron | 0.04354 | 1.068 (0.27-4.19) |
| 8 | SNP_A-1841568 | rs4945261 | 77667908 | GAB2 | intron | 0.04202 | 0.36 (0.061-2.12) |
| 12 | SNP_A-1826565 | rs7101429 | 77670615 | GAB2 | intron | 0.0187 | 0.77 (0.22-2.68) |
| 23 | SNP_A-2112731 | rs10793294 | 77674051 | GAB2 | intron | 0.01339 | 0.38 (0.087-1.64) |
| 5 | SNP_A-2153680 | rs4291702 | 77678896 | GAB2 | intron | 0.02438 | 1.068 (0.27-4.19) |
| 4 | SNP_A-2313615 | rs7115850 | 77722719 | GAB2 | intron | 0.03906 | 0.36 (0.061-2.12) |
| 2 | SNP_A-2012255 | rs2373115 | 77768798 | GAB2 | intron | 0.03906 | 0.36 (0.061-2.12) |
| | | | | | REPLICATION 2 COHORT | | |
| 10 | SNP_A-2208459 | rs901104 | 77608147 | GAB2 | intron | 0.1468 | 0.48 (0.17-1.31) |
| 3 | SNP_A-4215188 | rs1385600 | 77613814 | GAB2 | CDS--synonymous | 0.04632 | 0.18 (0.030-1.12) |
| 7 | SNP_A-2012248 | rs1007837 | 77618724 | GAB2 | intron | 0.2044 | 0.53 (0.20-1.42) |
| 16 | SNP_A-1882998 | rs2510038 | 77643682 | GAB2 | intron | 0.1468 | 0.48 (0.18-1.31) |
| 8 | SNP_A-1841568 | rs4945261 | 77667908 | GAB2 | intron | 0.04632 | 0.18 (0.030-1.12) |
| 12 | SNP_A-1826565 | rs7101429 | 77670615 | GAB2 | intron | 0.04992 | 0.40 (0.16-1.02) |
| 23 | SNP_A-2112731 | rs10793294 | 77674051 | GAB2 | intron | 0.02172 | 0.22 (0.059-0.85) |
| 5 | SNP_A-2153680 | rs4291702 | 77678896 | GAB2 | intron | 0.2044 | 0.53 (0.20-1.42) |
| 4 | SNP_A-2313615 | rs7115850 | 77722719 | GAB2 | intron | 0.003451 | 0.067 (0.0071-0.62) |
| 2 | SNP_A-2012255 | rs2373115 | 77768798 | GAB2 | intron | 0.003451 | 0.067 (0.0071-0.62) |

Example 3

High-Density Genome-Wide Association Study Specifics

Individualized genome-wide surveys were performed in a "neuropathological discovery cohort" of 749 expired brain donors, a "neuropathological replication cohort" of 307 expired brain donors, and an additional "clinical replication cohort" of 369 living subjects who were at least 65 years old at the time of their death or last clinical assessment and who were independently assessed for their APOE genotype. For the two neuropathological cohorts, brain tissue for DNA extraction, neuropathological diagnoses and data were supplied by investigators from twenty of the National Institute on Aging (NIA) sponsored Alzheimer's Disease Centers (ADCs) (in accordance with agreements with the NIA, the ADCs and the National Alzheimer's Coordinating Center) and from the Netherlands Brain Bank. 70% of the 1,056 expired LOAD cases and controls were randomly assigned to the hypothesis-generating neuropathological discovery cohort and the remaining 30% were assigned to the hypothesis-testing neuropathological replication cohort. For the hypothesis-testing clinical replication cohort, DNA extracted from blood, clinical diagnoses and data from subjects assessed in Rochester, Minn., were supplied by investigators from the Mayo Clinic.

The neuropathological discovery cohort included 454 LOAD cases (274 ε4 carriers and 180 ε4 non-carriers) and 295 controls (105 ε4 carriers and 190 ε4 non-carriers); the neuropathological replication cohort included 193 LOAD cases (102 ε4 carriers and 91 ε4 non-carriers) and 114 controls (27 ε4 carriers and 87 ε4 non-carriers); and the clinical replication cohort included 224 LOAD cases (117 ε4 carriers and 107 ε4 non-carriers) and 145 controls (28 ε4 carriers and 117 ε4 non-carriers). The expired brain donor cases satisfied clinical and neuropathological criteria for LOAD, and were age 73.5±6.2 at the time of death. The expired brain donor controls did not have significant cognitive impairment or significant neuropathological features of AD, and were age 75.8±7.5 at the time of death. The clinical cases satisfied criteria for probable AD, and were ages 78.9±7.8 at their last clinical visit. The clinical controls did not have clinically significant cognitive impairment and were age 81.7±6.6 at their last clinical assessment. APOE genotypes were obtained in each subject by either pyrosequencing (Ahmadian, supra) or restriction fragment length polymorphism (RFLP) analysis (Lai, supra).

The 500K GeneChip (Affymetrix, Santa Clara, Calif.) was used to survey 502,267 SNPs in each subject. Genotypes were extracted using both SNiPer-HD (Hua et al. (2007) *Bioinformatics* 23:57-63) and BRLMM (Affymetrix, Santa Clara, Calif.) software, and 321,953 SNPs were analyzed after excluding those that were monomorphic, did not cluster into three distinct Gaussian distributions, were associated with Hardy Weinberg equilibrium significance levels less than 0.01, had minor allele frequencies less than 3%, or exhibited less than 98% concordance between the SNiPer-HD and BRLMM calls. The software program STRUCTURE (supra) was employed to test for underlying genetic stratification, using 5,000 randomly selected SNPs and including at least 100 SNPs per chromosome. The initial analysis yielded empirical evidence of three populations. Since fourteen subjects belonged to a population far removed from the rest of the study population, they were eliminated from further analyses. STRUCTURE was used to demonstrate a comparable admixture of the two populations in the cases and controls. After stratifying the LOAD cases and controls for presence or absence of the APOE ε4 allele, allelic chi squares were computed for each SNP.

Figure 9:
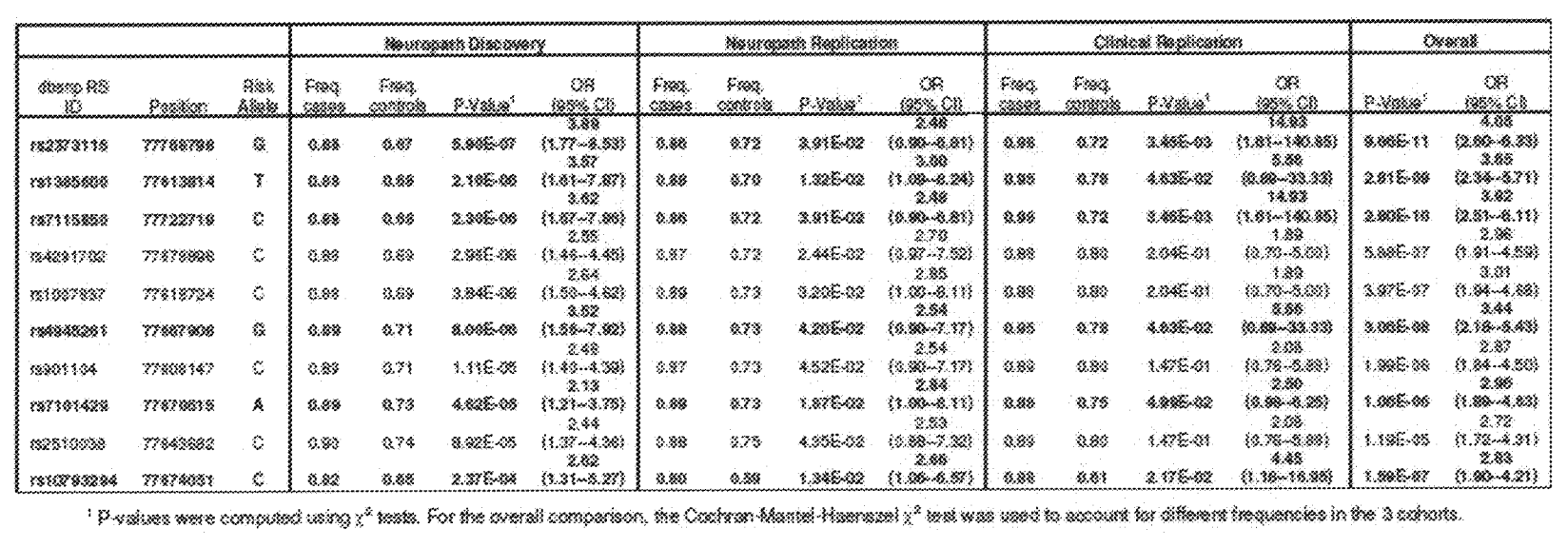

The inventors initially surveyed SNPs in the neuropathological cohort to explore LOAD associations in the ε4 carrier and non-carrier sub-groups. Within the discovery sub-group of APOE ε4 carriers, ten of the twenty-five SNPs with the most significant LOAD-association significance levels (p=2× $10^{-4}$ to $6\times10^{-7}$) were located in the GRB-associated binding protein 2 (GAB2) gene on chromosome 11q14.1 (see FIG. 9). LOAD associations in six of these SNPs were confirmed in both the neuropathological replication and clinical replication cohorts (FIG. 9). These ten SNPs were not significantly associated with LOAD in the APOE ∈4 non-carrier group (p=0.08 to 0.97). Combining data from all 653 APOE ∈4-carrying cases and controls, we found highly significant associations between LOAD and all 10 GAB2 alleles (p-values $1.19\times10^{-5}$ to $9.66\times10^{-11}$), with 5 of the 6 consistently implicated alleles surviving the highly conservative Bonferroni correction for 321,953 independent comparisons (FIG. 9).

Haploview v3.32 was used to determine the linkage disequilibrium (LD) structure of the chromosome 11q14.1 region surrounding GAB2 in each of the three APOE ∈4-stratified cohorts (FIG. 1). Three haplotype blocks are present in this region: one block upstream of GAB2, roughly corresponding to the ALG8 locus; one 189 kilobase-pair block encompassing most of the GAB2 locus; and one downstream block corresponding to the NARS2 locus. These blocks were consistent with the LD structure of the HapMap CEPH populations. The GAB2 gene is completely encompassed by this single haplotype block, which has three major haplotypes: an extremely common "GAB2 risk haplotype," a common "GAB2 protective haplotype," and a relatively uncommon GAB2 haplotype unrelated to LOAD risk in APOE c4 carriers (FIG. 1). In all three cohorts, the GAB2 CT-AAG-CAGATCAGACG (SEQ ID NO:2) haplotype was associated with higher LOAD risk, the GAB2 TC-GCA-TGAGGTGTCTT (SEQ ID NO:1) haplotype was associated with a lower LOAD risk, and the TA-T-GGA was unrelated to LOAD risk in the APOE ∈4 carriers (FIG. 9). The association between the NARS2 haplotype and decreased LOAD risk in two of the cohorts appears to be attributable to moderate LD between the NARS2 and GAB2 blocks.

Data from the 1425 subjects (including 653 APOE ∈4 carriers and 772 non-carriers) in all three cohorts were combined to characterize odds ratios (ORs) and 95% confidence intervals (CIs) for GAB2 risk haplotype homozygotes (see Table 6 below) and GAB2 protective haplotype carriers.

higher LOAD risk than the other ∈4 non-carriers (OR 1.01, 95% CI 0.73-1.38, P=0.97) and 64 non-carriers with the GAB2 protective haplotype did not have a lower LOAD risk than the other ∈4 non-carriers (OR 1.05, 95% CI 0.74-1.50, P=0.79). Whereas the inventors confirmed a younger age at dementia onset in the APOE 64 carriers than in non-carriers (age 80.8±7.7 versus 86.0±7.5, P=$3.8\times10^{-8}$), there was no significant GAB2 haplotype effect on age at dementia onset in either the 64 carriers (P=0.32) or non-carriers (P=0.84). Hence, the effects of GAB2 on LOAD risk most likely depends on both the ∈4 allele and a person's age.

Example 4

Identification of a Protective GAB2 Haplotype in LOAD

Haploview v3.32 was used to determine the linkage disequilibrium (LD) structure of the region on chromosome 11q14.1 surrounding GAB2 for each of the three APOE ∈4-stratified cohorts (discovery, replication 1, and replication 2; see FIG. 1). Three haplotype blocks are present in this region, one upstream of GAB2, roughly corresponding to the ALG8 locus, one 189 kilo-base pairs (kb) block encompassing most of the GAB2 locus and one downstream block corresponding to the NARS2 locus. These blocks are consistent with the LD structure of the HapMap CEPH populations. The GAB2 haplotype CT-AAG-CAGATCAGACG (SEQ ID NO:2) increases LOAD risk in all populations, although most strongly in the "replication 2" cohort (see Table 3 below). This is a surprising finding since this haplotype is common, being present in 67-78% of the individuals across our three separate study populations. The haplotype defined by TC-GCA-TGAGGTGTCTT (SEQ ID NO:1) shows a strong protective effect in the "discovery" and "replication 1" cohorts and is trending toward a protective effect in the "replication 2" cohort (see Table 3 below). Moderate LD exists between

TABLE 6

| APOE ∈4 Group | APOE ∈4 Group OR | GAB2 risk haplotype dose | Controls (N) | Cases (N) | % LOAD | OR[1] (95% CI) GAB2 vs entire ∈4 group | OR[2] (95% CI) | OR[3] (95% CI) GAB2 HM vs Non-HM in the ∈4 group[2] |
|---|---|---|---|---|---|---|---|---|
| Non-Carriers | 1.00 | 0-1 | 130 | 110 | 45.8% | 0.99 (0.74-1.34) | 0.99 (0.74-1.34) | 1.01 (0.73-1.38) |
| | | 2 | 222 | 189 | 46.0% | 1.00 (0.78-1.28) | 1.00 (0.78-1.28) | |
| Carriers | 6.07 (4.63-7.95) | 0-1 | 53 | 157 | 74.8% | 0.57 (0.39-0.84) | 3.45 (1.81-6.68) | 2.70 (1.72-4.73) |
| | | 2 | 41 | 328 | 88.9% | 1.55 (1.04-2.30) | 9.41 (4.82-18.29) | |

[1]OR in comparison with all of the subjects from the same APOE ∈4 carrier or non-carrier group.
[2]OR in comparison subjects carrying no copies of the APOE ∈4 allele and fewer than 2 copies of the GAB2 risk haplotype.
[3]OR of GAB2 risk haplotype homozygotes (HM) in comparison with the non-homozygotes from the same APOE ∈4 carrier or non-carrier group.

In ∈4 carriers, 67% of the LOAD cases and 43% of the controls were homozygous for the GAB2 risk haplotype. In comparison with the other ∈4 carriers, GAB2 risk haplotype homozygotes had a significantly higher risk of LOAD (OR 2.70, 95% CI 1.72-4.73, P=$9.4\times10^{-6}$). Indeed, 78 out of 79 persons (98.7%) homozygous for both the ∈4 allele and the GAB2 risk haplotype had LOAD, a significantly higher proportion than the 35 out of 39 APOE ∈4 homozygotes (89.7%) with fewer than 2 copies of the GAB2 risk haplotype (P=0.023). Within the same APOE ∈4 carrier group, 22% of the LOAD cases and 49% of the controls had at least one copy of the GAB2 protective haplotype. In comparison with the other ∈4 carriers, carriers of the GAB2 protective haplotype had a significantly lower risk of LOAD (OR 0.37, 95% CI 0.23-0.59, P=$1.5\times10^{-6}$). In contrast, APOE ∈4 non-carriers homozygous for the GAB2 risk haplotype did not have a the GAB2 block and the NARS2 block in all three populations, but is greatest in the "replication 2" cohort. This LD accounts for the significance of the TATGGA NARS2 haplotype in the "discovery" cohort, and the trend toward significance in the 'replication 1' cohort.

TABLE 3

| GAB2 haplotype block | GAB2 haplotype block |
|---|---|
| CT-AAG-CAGATCAGACG SEQ ID NO: 2 | TC-GCA-TGAGGTGTCTT SEQ ID NO: 1 |
| Increases LOAD risk. | Decreases LOAD risk. |

Example 5

Arrangement of SNPs

FIG. 8 provides additional details on each SNPs 5-22 in each of the GAB2 haplotypes including location and strand.

Example 6

Neuronal Microarray Studies

In order to provide converging evidence that GAB2 is biologically relevant to AD neuropathology, the inventors analyzed data from a neuronal microarray study of LOAD cases and controls. Expression profiling using the Affymetrix Human Genome U133 Plus 2.0 array was used to characterize and compare GAB2 expression in laser-capture microdissected non-tangle bearing neurons of cases and controls in six brain regions differentially affected by AD. LOAD cases had significantly greater neuronal GAB2 expression in the posterior cingulate cortex (9 cases, 13 controls, 4.50-fold change, P=0.00039) and hippocampus (9 cases, 13 controls, 2.94-fold change, P=0.00085), and no significant differences in the entorhinal cortex (10 cases, 13 controls, 1.20-fold change, P=0.46), middle temporal gyrus (13 cases, 12 controls, 1.44-fold change, P=0.14), superior frontal gyrus (22 cases, 11 controls, 1.25-fold change, P=0.47), or primary visual cortex (17 cases, 12 controls, 1.53-fold change, P=0.14).

The hippocampus is especially vulnerable to AD-related neurofibrillary tangles (Braak et al. (1991) Acta. Neuropathol. 82:239-259), neuronal loss and brain atrophy (Bobinski et al. (2000) Neuroscience 95:721-725). It is preferentially involved in AD-related memory impairment (Jack et al. (1999) Neurology 52:1397-1403) and is associated with the highest cerebral GAB2 expression in the rodent brain (Lein et al. (2007) Nature 445:160-161). The posterior cingulate cortex is vulnerable to AD-related hypometabolic abnormalities and fibrillar amyloid deposition, and is also involved in AD-related memory impairment. While the entorhinal cortex, temporal and prefrontal regions are also affected by AD neuropathology, the visual cortex is relatively spared. Using a repeated measures analysis of variance to analyze neuronal GAB2 gene expression data from the same 8 LOAD cases and 10 controls, there was a significant group-by-region interaction (P=0.011), with LOAD-related increases in neuronal GAB2 gene expression that were greater in the posterior cingulate cortex and hippocampus than in the visual cortex.

Example 7

Immunohistochemical Validation

Figure 4:
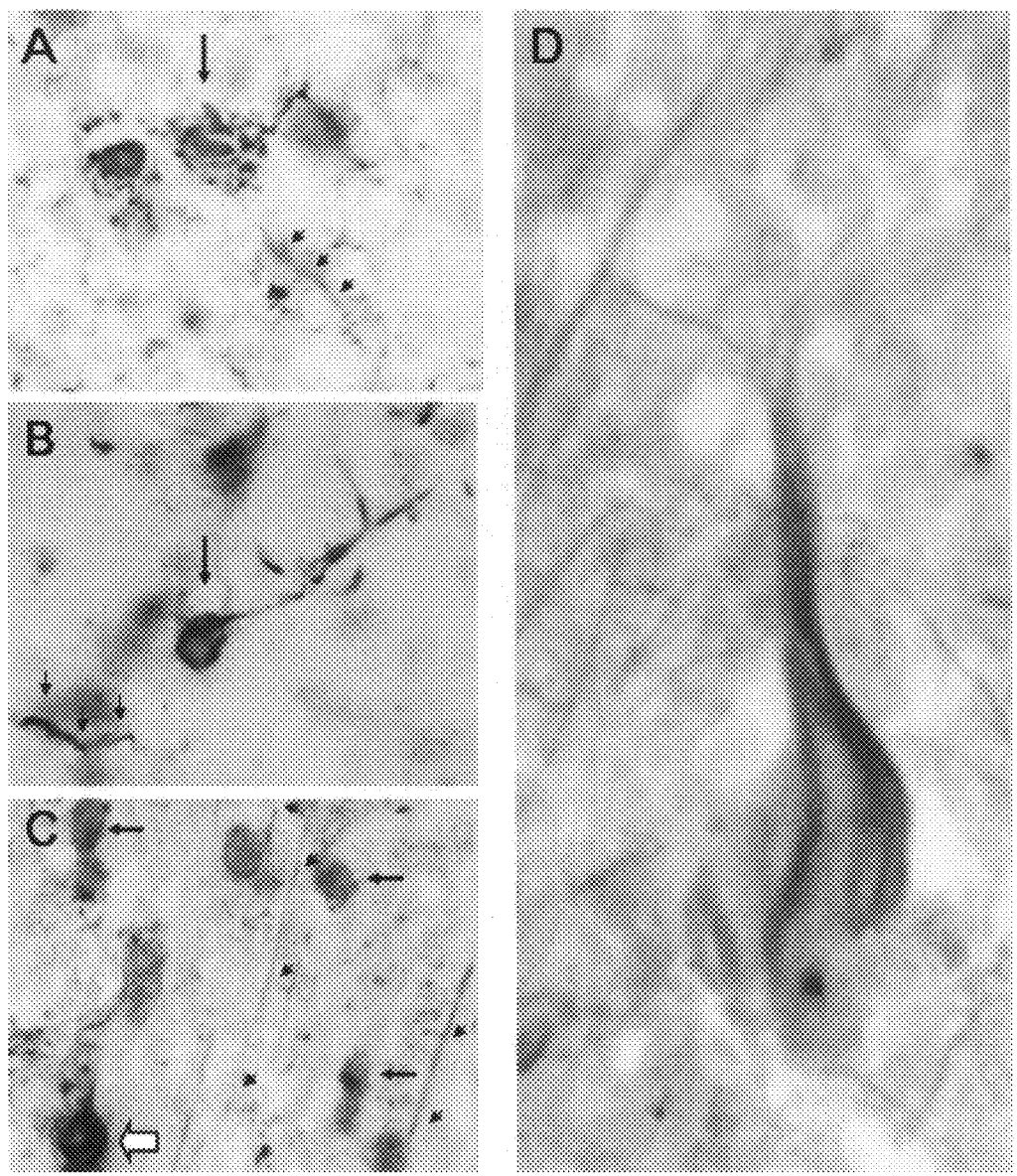

In order to show neuronal expression of GAB2 at the protein level, GAB2 immunohistochemistry was assessed in LOAD hippocampus and posterior cingulate cortex in LOAD cases. In hippocampus, GAB2 immunoreactivity was observed in structures with the morphology of dystrophic neurites or neuropil threads, neurons, and corpora amylacea. The putative neurons were almost entirely dystrophic in appearance (FIG. 4A) or had cytoplasmic inclusions resembling neurofibrillary tangles (FIG. 4B). Dystrophic neurons and neurites (FIG. 4C) and neurofibrillary tangle bearing cells (FIG. 4D) were also revealed by the GAB2 antibody in posterior cingulate. Here, however, many relatively normal neurons were observed as well, with long stretches of immunoreactive apical dendrites ascending through the cortical layers (FIGS. 4C and 4D).

Example 8 siRNA Study

In addition to its other properties, GAB2 is the principal activator of the phosphatidylinositol 3-kinase (PI3K) signaling pathway (Pratt et al. (2001) J. Immunol. 165:4158-4163). PI3K activates Akt, which in turn promotes glycogen synthase kinase-3 (GSK-3) phosphorylation/inactivation, suppressing GSK-3-dependent phosphorylation of tau at AD-related hyperphosphorylated tau residues, the principal component of neurofibrillary tangles, and preventing apoptosis of confluent cells (Baki et al. (2004) EMBO J. 23:2586-2596; Kang et al. (2005) J. Biol. Chem. 208:31537-31547). Based on this relationship, GAB2 could function to protect cells from neuronal tangle formation and cell death and a loss-of-function GAB2 haplotype would lose some of this protection function. Thus, interference with GAB2 expression using siRNA treatment would increase tau expression at the serine-262 residue known to be hyperphosphorylated in AD.

Figure 5:
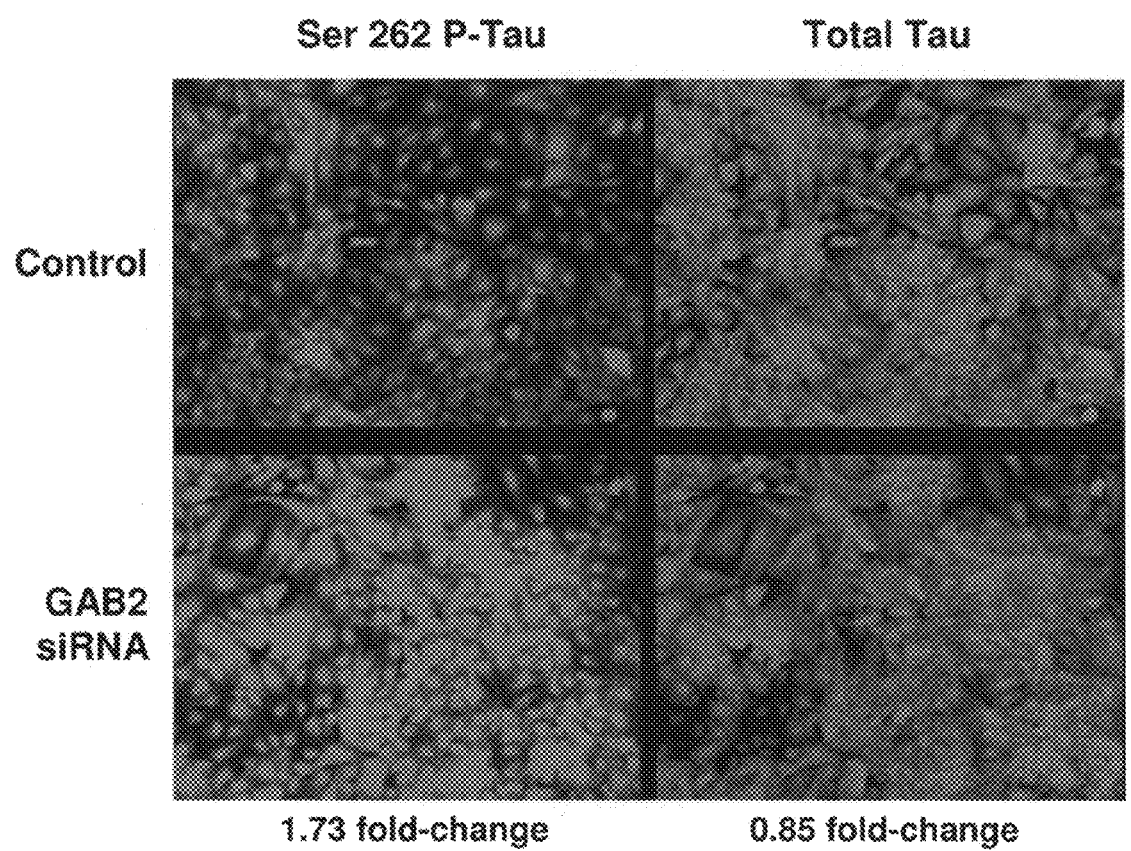

Neuroglioma cells overexpressing tau protein were grown in 96-well plates and transfected with siRNA directed at GAB2 mRNA. Following four days of transfection, cells were fixed, permeablized, and immunostained with antibodies against total tau protein and tau protein phosphorylated on serine-262. A FITC- and CyS-conjugated secondary antibody cocktail was then applied. After incubation and washing, images were captured and quantitated using the InCell imager 3000 (General Electric). The fold increase in serine-262 phosphorylated tau levels was calculated against control samples that had been transfected with a scrambled siRNA sequence. As shown in FIG. 5, GAB2 siRNA treatment was associated with a 1.70-fold increase in serine-262 phosphorylated tau, and the apparent increase did not appear to be attributable to an increase in total tau levels. Additional siRNA and protein validation studies are performed to confirm this finding (data not shown).

Example 9

Summary of Findings

The present inventors were able to use their genome-wide survey of more than 500,000 SNPs, two unusually large clinically characterized and neuropathologically verified cohorts of AD cases and controls, a third cohort of clinically well characterized subjects, and stratification of the samples carriers and non-carriers of a major susceptibility gene to characterize and confirm associations between the GAB2 gene and LOAD risk in APOE ε4 carriers. Six SNPs and a common haplotype block encompassing the entire GAB2 gene were implicated in three independent cohorts. The data from the microarray study of laser-capture microdissected neurons in LOAD cases and controls, immunohistochemistry, and a siRNA study provided converging evidence for the relevance of GAB2 to the neuropathology of LOAD. This allows the inventors to link to a mechanism by which GAB2 can modify LOAD risk in ε4 carriers and thus, provide targets at which to aim new treatments.

Figure 6:
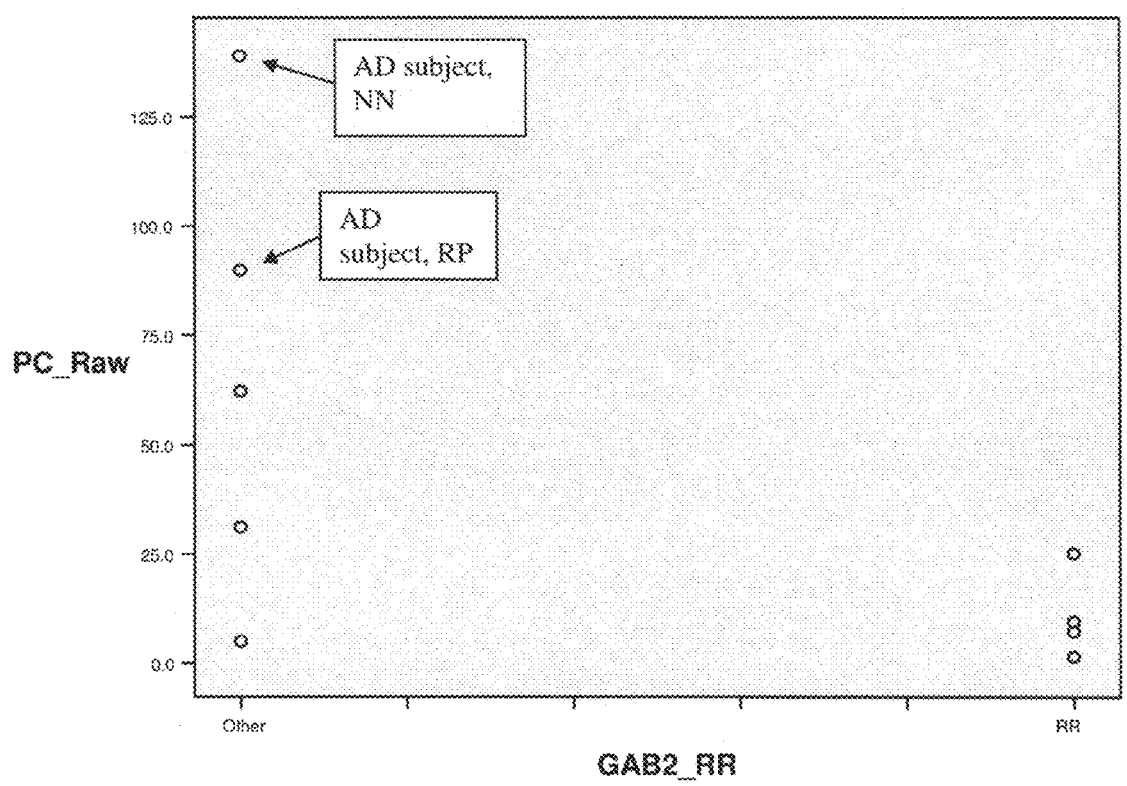

Although only one genotyping platform was used in all three cohorts, the inventor's findings are unlikely to be attributable to any platform-related bias in genotyping calls since the observed association was not limited to a single SNP but was related to a large haplotype block in agreement with the LD structure of the HapMap CEPH population. Further, all six of the implicated scores had high-quality SNiPer-HD scores (greater than 0.45), indicating that the data for each SNP clustered into three distinct Gaussian distributions corresponding to the three possible genotype calls. While GAB2 haplotypes were characterized in only a few of the subjects from the microarray studies, inspection of posterior cingulate GAB2 gene expression in the three GAB2-characterized controls homozygous for the risk haplotype (10.8±10.1 raw expression units) and the three GAB2-characterized non-homozygous controls (32.8±28.6 raw expression units) support that GAB2 is under-expressed in GAB2 risk haplotype homozygotes (See also, FIG. 6).

GAB2 is a scaffolding protein involved in multiple signaling pathways, which can affect AD-related tau, amyloid, metabolic, or other aspects of AD pathology and cell survival. Thus, discovery of this novel LOAD susceptibility gene provides new opportunities to investigate LOAD pathogenesis, predisposition, treatment and prevention.

Various modifications and variations of the present disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure which are understood by those skilled in the art are intended to be within the scope of the claims.

Example 10

Additional Markers

Genetically complex phenotypes and diseases result from the interplay between genetic variants and environmental factors. Despite this fact, most genetic association studies to date have either evaluated one genetic variation at a time or have analyzed multiple variations independently. However, this approach ignores the polygenic nature of the studied phenotypes, focuses on marginal gene effects, inflates the probability of type I error, and erroneously assumes that the impact of the variation under study is comparable to a major gene effect. Recent developments in high-throughput genotyping and computerized algorithms now facilitate multi-locus analyses for the localization of complex trait genes and clusters thereof. As shown for schizophrenia and Alzheimer's disease, multi-locus analyses acknowledge the polygenic nature of disease, provide sets of trait-associated markers and also control for multiple testing. Importantly, such analyses may provide individual genetic clusters with potentially important clinical implications for future diagnosis, prognosis, and personalized treatments.

One of the recently used data-reduction methods which yields clusters of genes related to the phenotype of interest and which has already worked well in our hands is the set-association method. It uses relevant sources of genetic information, such as allelic association and Hardy-Weinberg disequilibrium (HWD). Information is combined over multiple markers and genes in the genome, quality control is improved by trimming SNPs with high HWD values, and permutation testing limits the overall false-positive rate. For each candidate marker, two chi-square statistics were computed: one for the allelic association with disease status and one for HWD in cases. The products of these statistics for each marker are then ranked from largest to smallest. Progressively larger sums ($S_j$) are then calculated over the j largest chi-square statistics. For example, S1 is the largest chi-square statistic of association. S2 is the sum of the largest and second largest. S3 is the sum of the largest, second largest and third largest, etc. The empirical significance level (Pj) for each Sj is evaluated by permutation methods carried-out under the null hypothesis of no genetic association with LOAD. The smallest of the empirical significance levels (i.e. Pjmin) identifies the best and most parsimonious model predicting disease status. Importantly, the set-association method has been shown to be of superior power compared with conventional locus-by-locus analyzes and to successfully capture statistical interactions between genes.

This set-association method was applied to the hypothesis-free whole-genome association study described in the previous examples, which utilized the Affymetrix 550K SNPchip in 593 histopathologically verified AD cases and 320 histopathologically verified controls. To minimize the possibility of type I errors, cases and controls were a priori and randomly separated in two samples: 70% of cases and controls composed a hypothesis-generating sample (i.e., the set-association method including the generation of a SNP cluster was applied in this sample), whereas the remaining 30% were used as a hypothesis-testing sample to evaluate independently the significance of the SNP cluster. After removing SNPs with low call rates, the top 1000 SNPs of the hypothesis-generating sample, as assessed by their genotypic P-value for association with AD in single-locus $\chi^2$ tests, were included in the set-association procedure. A cluster of 20 SNPs (including APOE) was significantly ($P<10^{-10}$) associated with LOAD and was then used for the generation of a composite cluster score, which was based upon the combined set-association statistic for each of the 20 cluster SNPs. Table 7 shows the SNPs excluding APOE. Thus, the score corresponded to the number of individual risk alleles weighted by the contribution (i.e. effect size) of each risk allele to the overall cluster. The genetic score of individuals not carrying any risk allele was set equal to 0, which is the minimal possible score value. Accordingly, the score of individuals possessing one risk allele was set equal to the corresponding set-association statistic for the particular SNP. For two or more risk alleles, set-association statistics of the corresponding SNPs were added.

Figure 7A:
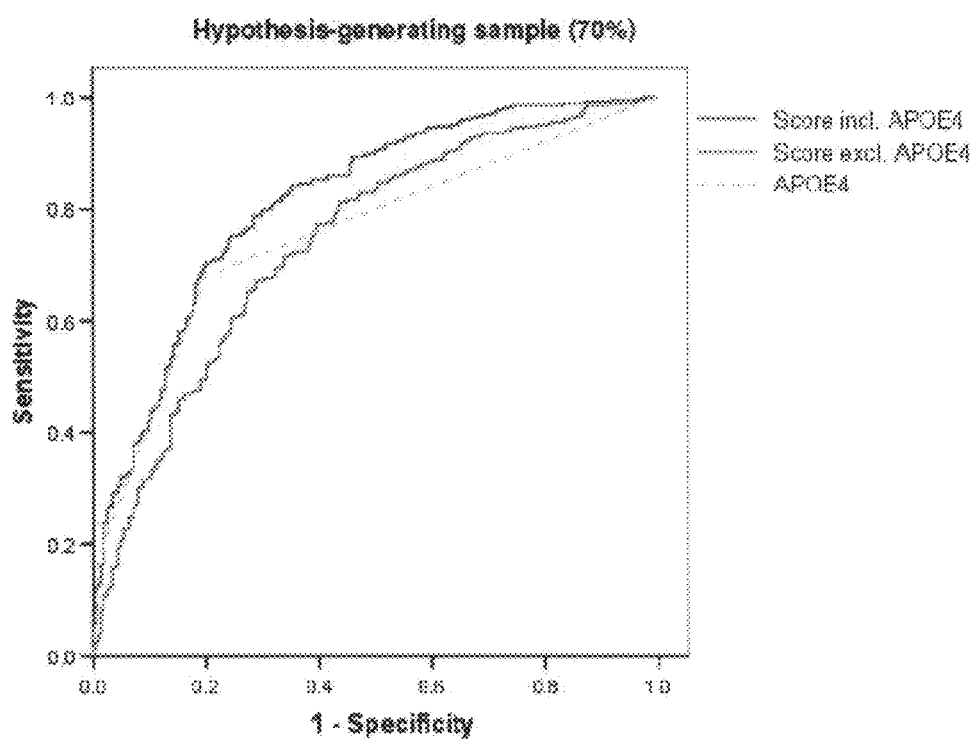
FIG. 7 shows (A) the ROC analysis of the discriminatory ability between cases and controls for the hypothesis-generating sample, and (B) the ROC analysis of the discriminatory ability between cases and controls for hypothesis-testing sample.
Figure 7B:
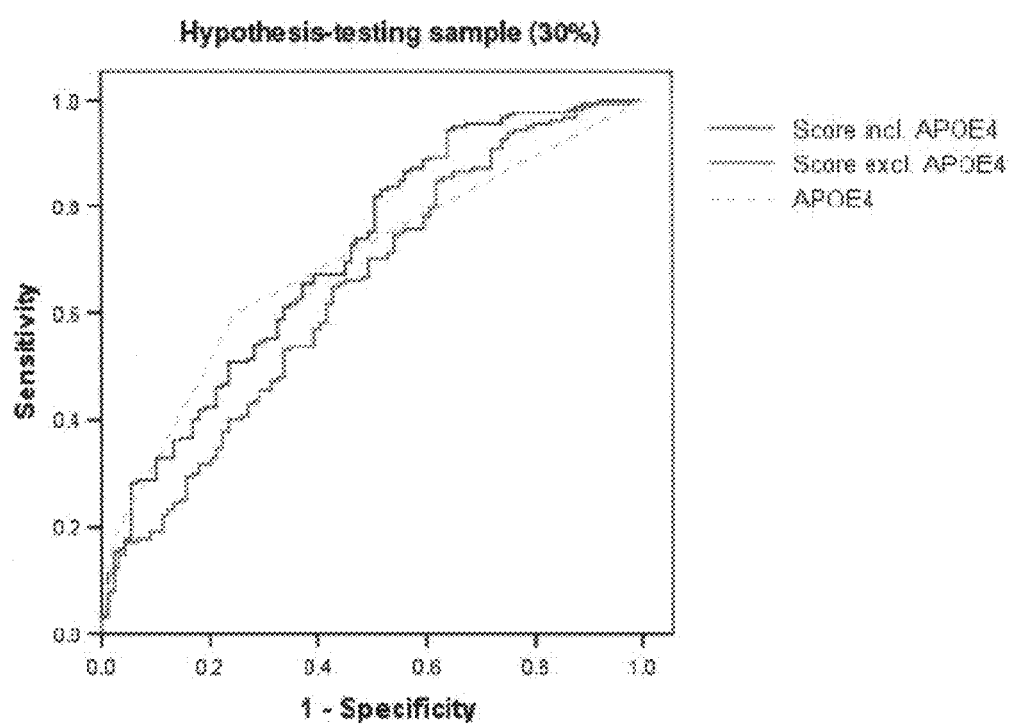

In the hypothesis-generating sample, AD patients (n=407) had a mean score (±SD) of 429±108, the score of the controls (n=224) was 300±97 ($P<10^{-10}$). The discriminatory ability between cases and controls (as assessed by ROC analysis, See FIG. 7A) was 81%. When APOE was excluded from the score, AD patients had a mean score of 367±96, the score of the controls was 284±91 ($P<10^{-10}$). The discriminatory ability was 74%, that of APOE4 allele alone was 75%. The above observations were confirmed in the smaller, 30% hypothesis-testing sample: AD patients (n=177) had amean score of 424±115, the score of the controls (n=89) was 329±116 ($P=6*10^{-10}$). The discriminatory ability between cases and controls (as assessed by ROC analysis, See FIG. 7B) was 71%. When APOE was excluded from the score, AD patients had a mean score of 368±103, the score of the controls was 306±103 (P=2*10-6). The discriminatory ability was 64%, that of APOE4 allele alone was 69%. Importantly, SNPs in linkage disequilibrium with the APOE4 locus were excluded from the cluster.

ADDITIONAL SEQUENCES

```
SEQ ID NO: 4 - nucleic acid sequence for human GAB2: 6006 bp
    1 atgagcggcg gcggcgacgt ggtgtgcacc ggctggctga ggaaatcgcc tcccgagaag 61 aagttgaggc gctatgcctg gaagaaacgc tggtttatcc tgcggagtgg ccggatgagc 121 ggtgacccag atgttctgga atactacaag aacgatcact ccaagaagcc tctgcggatc 181 atcaacctga acttctgtga gcaggtagat gcaggcctga cctttaacaa gaaggagctg
```

-continued

```
 241 caggatagtt ttgtgtttga catcaagacc agtgaacgca ccttttacct ggtggctgag
 301 acagaagagg acatgaataa gtgggtccag agcatctgcc agatctgtgg cttcaatcag
 361 gctgaggaga gcacagactc cctgagaaat gtttcctcag ccggtcatgg ccccgctct
 421 tctccagctg agctcagcag ctctagccac caccttctcc gagagcgcaa gtcctcagcc
 481 ccatcacact ccagccagcc aactctgttc acgtttgaac ccctgtgtc aaaccacatg
 541 cagcccacct tgtccaccag cgcacctcag gagtatctct acttgcacca gtgcataagc
 601 cgaagagcag aaaatgcaag gagtgccagc ttctctcagg gcaccagagc ctcttttctc
 661 atgaggagtg acacagctgt acaaaaactt gcccagggca atggacactg tgtcaacggg
 721 atcagtggtc aagtccatgg cttctatagc cttcccaagc cgagccggca caatacagaa
 781 ttcagagaca gtacctacga cctccccgc agcctggcct ccatggcca caccaagggc
 841 agcctcacag gctccgagac agataatgag gatgtgtaca ccttcaagac gcccagcaac
 901 accctgtgca gggagttcgg ggacctcctg gtagacaata tggatgttcc ggccacccca
 961 ctctcagcct accagatccc taggacattc actctggaca aaaaccacaa tgccatgaca
1021 gtggccactc ctggggactc agccatagct ccccacccc gccccccaa gccaagtcag
1081 gcagaaacac ctcgatgggg cagtcctcag cagagaccgc caatcagtga aaatagcaga
1141 tctgtcgctg ccaccatccc cagacgcaac accctccctg caatggacaa cagccgactt
1201 caccgagctt cttcctgtga gacctacgag tacccacacg gtggtggaga gagtgcaggc
1261 cggtctgctg aatccatgag tgatggagtt ggctcttttcc tgccagggaa aatgattgtg
1321 ggccgatcgg acagcaccaa ttctgaagac aactatgtgc ccatgaatcc aggttcttcc
1381 accctgttgg ccatggaacg agcaggtgat aattcccaga gcgtctacat cccaatgagc
1441 ccaggggccc atcactttga ctcacttggc tacccatcaa caacccttcc tgtgcaccga
1501 ggccccagca gaggaagtga gattcagcca ccccctgtca accgcaacct caaacctgat
1561 cggaaagcaa agccaaccac acttgacctg aggaacaaca ccgtcatcga tgaactcccc
1621 ttcaagtcac ctatcaccaa gtcttggtct agggccaacc acaccttcaa ctccagctcc
1681 tcccagtact gccgcccat ctccacccag agcatcacca gcacagactc aggagacagc
1741 gaagagaact atgtccctat gcaaaaccca gtgtctgcat ctcccgttcc cagtggcacg
1801 aacagtcctg cccctaagaa gagcaccggc agcgttgatt atctggccct ggacttccag
1861 ccgagctccc caagccccca ccgcaagcca tctacttcat ccgtcacctc tgatgagaag
1921 gtggactacg ttcaggtgga caaggagaag acccaggccc tgcagaacac catgcaggag
1981 tggacagacg tgcggcagtc ctcagagcct tccaagggtg ccaagctgtg atgagagggc
2041 caccgcagag cccaggaggc agcatctcca gagctggccc ttcccatctc ccctctcccc
2101 tctcccgttc ttcctcccat ccacctcctc tctactctgc cagtctcagc cttcaaagca
2161 cttgacatca gggaccctga acccttcccc tgggaggtga gggcctgatc aaggcacctc
2221 ctctgcccac tcggggccca gctgtgattt ttatcagtaa tggccatgcc tccacccacc
2281 ttagttagga gctacttcca aaagcatcc ttcagcctct tcctgtcctt tagacctgac
2341 tctctaccag atgtttggag ggaagggctg gggctctgag ccagattcca cacctcacgt
2401 tcagtcacag ccctcagcta tcttccctcc ggccactggg ctacctctcc ttcagtccca
2461 gaagacaagt ctcaccaacc cagggagtca aggaccagca aaccaaagtg gataatggac
2521 tttttcattc ctgttttttct tggcaggaga gaagcaaggc cactaaaaga ggagatggtg
2581 gagacggagg ctcagcagtg gtcttgaggg gtaaaggact tagatgccca gatgaagagg
2641 gaaagctgac atctgcaggg aacccacttt gaggctgagg ccatggcagg acagctgctg
```

-continued

```
2701 tggggtgcag aggcagaaga tgaaggacaa aaggaaggga aaactgatgg ccaacctaga
2761 gcagcaagga gcagggcttg gagctcgggt ggtggagatg acaaggacac tgtgggtct
2821 gggtccccag aactctggag ctacaggcca ctctaggccc aagggctagt cctcttcccc
2881 agtcccctca gaggcccccg ccagcccac cttgaaagca gcatacaggg gaaggcttgg
2941 accaagctgg gcgaccaagc acatgggca ggaacacatg gtaaaggggt ggggaatatg
3001 ggagggagtg tggtgtggat ggggtgatg cagggactga ggggaaccct gggacaggca
3061 caggctgggc agaggcacag ggcagtgcag gggactctgc agtggggtcg ggaagtgagt
3121 ttctttgcag tgagcagtgc agtggaagtc gggcacagag gtagcagaca gatgtgaagc
3181 agtggtgaag gccatgtagc aagtgggaa atacatccaa agggcctggg agttgggggg
3241 tgcccaacgc aatccttggg ggtgcagggt ggagcagaaa gtgaaggagg acacgtgca
3301 agagtggtgt gcatggtggt gtgacatgag gaccgttcct aggatgggac agtgggtcag
3361 gcaggacaag gagaaagcag ggcagaatga tgcctagagg accacatcag gcatggctga
3421 cagcttgtgc ccatgggctg tggcgtatgt cagatcgcag ggtaggaacg agtctggcct
3481 ggtgccggcc cagtgtttcc tcagctcatc cgccctctgt tgctccctag cattacagga
3541 gccatcttgg actctcctcc ccaggtttga aaggccatca gattagcagg gacgggtgt
3601 agggcatcac ccaaggttcc ttctcttaaa ctaagggtgg gggatctgaa tgtttttatg
3661 ttgactgttc ttgactaaat tttcaagagt ttcagaagca acaggacaga ccagacgttt
3721 cattctaccc tggggcgaac agaacttctt cctcccaaac aatgacttcc tgccatgttt
3781 gatgggaca gctaccactg tcctctgccc ccattcccct ttcagctccc atgagcatgc
3841 atagttcacc agaccaatgg cctagccatt ctctaagtcc catcctggaa gaagttatt
3901 cttcaagagc tgcacctctc ctcctagcat tagtttagat caactcaagg agtatttatt
3961 aatggctgct gtctccagtt tctggggtta agcactaagg acacaagaat caatcagacc
4021 ttctccctga acttaagata gccacaatca gaaaaaggac aaggacatga gacagtggtg
4081 atggccatca gacagagact tcaaatgctg atggagggca gaggaagtac ttagggaggt
4141 tggtgtcaga ggcaggagtg ggggatcagg gaaggtggat tctaggaaaa gggagtgcct
4201 gaggtaggcc ttagaagggg atgagtcaga ttttacaga ggaggagggc agggcttggg
4261 tccagtggag gaagaaggaa ggagaggctt ggaaagcctt tgtgtcttggg aaaaaaaggc
4321 ctttgagcat atgggtccag ccactcagaa gtgcaggggc catgccttgg tgttccaata
4381 agtgaatgga agcagtggtg gtagctacac tgggcagagt tggcagggtg ctggttcact
4441 ctgcccagcc ctgaatgtgt gccttaaagg cccctacaa ggggcccat acgacagagc
4501 ttttaactgg tgccttccct gtacccgcag cagccacaag tgggcccaga ctattgcagc
4561 ctcccataaa catgtgagca tgttctgagt gtgccatgat gtgagtggac ctggctggaa
4621 tcttcggaga gcgactgagg tgttcaaatc gaatctccca ggaggcttcc ttccagcccc
4681 ctattctggt aactaccagg aggcttcctt ccagcccct attctggtaa ctaccaaaat
4741 ccctcgggtg caagtgtagg ggtagagatg gaaggatgag aggtgaaatt gacctttga
4801 aagcaaagct ctggctcaca ggccccaaac taccagccgt atctagcata tccccaccct
4861 ccacccacta cctcctccaa caaaggagtc aactcagttg aaaaaactgg tcctttggcc
4921 tatccatggg tcaaagtcca cctctcctgg gggcctggag aggactgagc ctacggaaag
4981 gggataccctt cccactcagc actgcttcac acaggccccc tgcctgggc tctccaagga
5041 gccttcttca cccacttcca gctccacttc tgcaaggtta agtcaagtga gaacgatgag
```

```
5101 aaatagggag atggtgtctc cttaagtcct tgatctgcct gtctgtggaa tgggaggttg 5161 gattagctgc gctgaggtcc catccacagc tggtgctcag ctgcttgaag gggagactcc 5221 ctcctctgta acttctttct gggggattgg ggtgggcagt acctatcccc agtccctcc 5281 tagcttgact ttagtggttt ccaatgtaga agttaacaaa gtatgcccca ttcctgtgac 5341 aaaagcacaa ccattctgaa gttactggag catgggctca gctcatcctc cctctggccc 5401 cttctcccat ggggacatct cggcccagca cccctatccc atttccagag ttcttccttc 5461 cccatctggg ccttcataaa atgcagggga agccagactg gtctcaggag cgctaaagcc 5521 cttccgtggg gggtcgtctt tctgggacta gccctgctgt ttaggacctg ggaccacaat 5581 ggggtacctg ccgaggggt ccccaagaga tccaggctgt catgtgattt atggtggcat 5641 gtgttgtgta tttgttggct acttgtgtct tgaaatctag aattatttca cgcagaattg 5701 tcactgtttg tcaggaagag aaaatgggct agtggaagcc cagtcttgag ttcttgtctt 5761 gttaccattt aaaattgaca tttaattttc aaatcactgt tggtgcctaa tcacttaagt 5821 tattaattta ttctgttgta ttcttttttt taaattgtaa catatttatc cggtgggtgg 5881 gacaggagtg tgttcaagtg ggtcatgttt ttgctgtggt gacacatggt acaggcttgg 5941 agcttgcagg tcccttttcta ctgtggtgtt ggagcaggac aataaagtcc actagaaatg 6001 cacccc SEQ ID NO: 5 - amino acid sequence for human GAB2: 1-676 amino acids
   1 msgggdvvct gwlrksppek klrryawkkr wfilrsgrms gdpdvleyyk ndhskkplri 61 inlnfceqvd agltfnkkel qdsfvfdikt sertfylvae teedmnkwvq sicqicgfnq 121 aeestdslrn vssaghgprs spaelsssq hllrerkssa pshssqptlf tfeppvsnhm 181 qptlstsapq eylylhqcis rraenarsas fsqgtrasfl mrsdtavqkl aqgnghcvng 241 isgqvhgfys lpkpsrhnte frdstydlpr slashghtkg sltgsetdne dvytfktpsn 301 tlcrefgdll vdnmdvpatp lsayqiprtf tldknhnamt vatpgdsaia ppprppkpsq 361 aetprwgspq qrppisensr svaatiprrn tlpamdnsrl hrasscetye ypqrggesag 421 rsaesmsdgv gsflpgkmiv grsdstnsed nyvpmnpgss tllameragd nsqsvyipms 481 pgahhfdslg ypsttlpvhr gpsrgseiqp ppvnrnlkpd rkakptpldl rnntvidelp 541 fkspitksws ranhtfnsss sqycrpistq sitstdsgds eenyvpmqnp vsaspvpsgt 601 nspapkkstg svdylaldfq psspsphrkp stssvtsdek vdyvqvdkek tqalqntmge 661 wtdvrqssep skgakl
```

TABLE 7

| Probe Set ID | dbSNP RS ID | Allele A | Allele B | Chr | Physical Position | Gene | Gene Relationship |
| --- | --- | --- | --- | --- | --- | --- | --- |
| SNP_A-1953700 | rs4650945 | A | G | 1 | 172350727 | RABGAP1L | upstream |
| SNP_A-4255838 | rs592228 | C | T | 1 | 227967134 | KIAA0133 | downstream |
| SNP_A-1840460 | rs866596 | C | T | 1 | 230213553 | DISC1 | intron |
| SNP_A-4248141 | rs10186622 | C | G | 2 | 174013281 | CDCA7 | downstream |
| SNP_A-2273653 | rs9844318 | G | T | 3 | 127101215 | LOC200810 | downstream |
| SNP_A-1860036 | rs17444609 | A | G | 5 | 24146110 | CDH10 | downstream |
| SNP_A-1825342 | rs11242704 | A | G | 6 | 1480997 | | |
| SNP_A-1892413 | rs7827093 | A | G | 8 | 22390555 | PPP3CC | intron |
| SNP_A-2089135 | rs10109855 | A | C | 8 | 34928318 | UNC5D | upstream |
| SNP_A-4268301 | rs7931291 | C | T | 11 | 14601002 | PSMA1 | intron |
| SNP_A-2009561 | rs271022 | C | T | 11 | 32664491 | CCDC73 | intron |
| SNP_A-2039029 | rs17093 | A | G | 11 | 45001765 | TP53I11 | upstream |
| SNP_A-2201646 | rs6591559 | C | T | 11 | 59782141 | MS4A4A | upstream |
| SNP_A-4268435 | rs3922568 | A | C | 12 | 34451374 | | |
| SNP_A-4249455 | rs2127955 | A | G | 12 | 36255461 | | |
| SNP_A-4274337 | rs2387836 | A | G | 12 | 36846337 | | |
| SNP_A-2109454 | rs249154 | C | G | 12 | 93848687 | NDUFA12 | downstream |

TABLE 7-continued

| Probe Set ID | dbSNP RS ID | Allele A | Allele B | Chr | Physical Position | Gene | Gene Relationship |
|---|---|---|---|---|---|---|---|
| SNP_A-1923247 | rs2553215 | G | T | 15 | 52797320 | C15orf15 | downstream |
| SNP_A-2183141 | rs17264732 | A | G | 16 | 84973089 | FOXF1 | upstream |

We claim:

1. A method of assigning a subject to a late onset Alzheimer's disease (LOAD) risk group, the method comprising:
   a.) providing a biological sample from the subject;
   b.) detecting, directly or indirectly, in the biological sample, a marker associated with a haplotype of GAB2 associated with LOAD; and
   c.) assigning the subject to the late onset Alzheimer's disease (LOAD) risk group based upon the presence or absence of the haplotype;
   wherein the subject is an APOE-ε4 carrier.

2. The method of claim 1, wherein the marker is associated with increased risk of LOAD and the subject is assigned to a high LOAD risk group if the subject has the marker.

3. The method of claim 2, wherein the marker is associated with the haplotype of GAB2 and is selected from the SNP haploblock identified by SEQ ID NO: 2.

4. The method of claim 1, wherein the haplotype of GAB2 is associated with decreased risk of LOAD and the subject is assigned to a low LOAD risk group if the subject has the haplotype of GAB2.

5. The method of claim 4, wherein the marker is associated with the haplotype of GAB2 and is selected from the SNP haploblock identified by SEQ ID NO: 1.

6. The method of claim 1, wherein the marker is detected by a method selected from the group consisting of nucleic acid hybridization, GAB2 antibody binding, and GAB2 activity assay.

7. The method of claim 6, wherein the marker is detected by nucleic acid hybridization using at least one hybridization probe specific to a SNP specific to the SNP haploblock identified by SEQ ID NO:1 or SEQ ID NO:2.

8. The method of claim 1, wherein the marker is detected by polymerase chain reaction (PCR).

9. The method of claim 1, wherein the marker is detected through a S1 nuclease assay.

10. The method of claim 1, wherein the marker is detected by a gene chip.

11. A method of assigning a subject to a late onset Alzheimer's disease (LOAD) risk group, the method comprising:
    a.) providing a biological sample from the subject;
    b.) detecting, directly or indirectly, in the biological sample, an APOE-ε4 allele and a marker associated with a haplotype of GAB2 associated with LOAD; and
    c.) assigning the subject to the late onset Alzheimer's disease (LOAD) risk group based upon the presence of the APOE-ε4 allele and the presence or absence of the hapoltype of GAB2.

12. The method of claim 11, wherein the marker is associated with increased risk of LOAD.

13. The method of claim 12, wherein the marker is associated with the haplotype of GAB2 and is selected from the SNP haploblock identified by SEQ ID NO: 2.

14. The method of claim 11, wherein the haplotype of GAB2 is associated with decreased risk of LOAD and the subject is assigned to a low LOAD risk group if the subject has the haplotype of GAB2.

15. The method of claim 11, wherein the marker is associated with the haplotype of GAB2 and is selected from the SNP haploblock identified by SEQ ID NO: 1.

16. The method of claim 11, wherein the marker is detected by a method selected from the group consisting of nucleic acid hybridization, GAB2 antibody binding, and GAB2 activity assay.

17. The method of claim 16, wherein the marker is detected by nucleic acid hybridization using at least one hybridization probe specific to a SNP specific to the SNP haploblock identified by SEQ ID NO:1 or SEQ ID NO:2.

18. The method of claim 11, wherein the marker is detected by polymerase chain reaction (PCR).

19. The method of claim 11, wherein the marker is detected through a S1 nuclease assay.

20. The method of claim 11, wherein the marker is detected by a gene chip.

* * * * *